United States Patent
Degen et al.

(10) Patent No.: US 10,716,922 B2
(45) Date of Patent: Jul. 21, 2020

(54) IMPLANTABLE FLUID MANAGEMENT SYSTEM HAVING CLOG RESISTANT CATHETERS, AND METHODS OF USING SAME

(71) Applicants: Sequana Medical NV, Zwijnaarde (BE); Christopher C. Bolten, San Diego, CA (US)

(72) Inventors: Thomas Werner Degen, Birmensdorf (CH); Noel L. Johnson, Saratoga, CA (US)

(73) Assignee: Sequana Medical NV, Zwijnaarde (BE)

( * ) Notice: Subject to any disclaimer, the term of this patent is extended or adjusted under 35 U.S.C. 154(b) by 521 days.

(21) Appl. No.: 15/249,192

(22) Filed: Aug. 26, 2016

(65) Prior Publication Data
US 2018/0056050 A1 Mar. 1, 2018

(51) Int. Cl.
*A61M 27/00* (2006.01)
*A61M 1/28* (2006.01)
(Continued)

(52) U.S. Cl.
CPC .......... *A61M 27/002* (2013.01); *A61M 1/285* (2013.01); *A61M 5/14276* (2013.01);
(Continued)

(58) Field of Classification Search
CPC .............. A61M 1/285; A61M 5/14276; A61M 25/0015; A61M 25/007; A61M 27/002;
(Continued)

(56) References Cited

U.S. PATENT DOCUMENTS 3,540,451 A  11/1970 Zenman
3,575,158 A   4/1971 Summers
(Continued)

FOREIGN PATENT DOCUMENTS

CN  101485683 A  7/2009
CN  201930383 U  8/2011
(Continued)

OTHER PUBLICATIONS

U.S. Appl. No. 15/985,617, filed May 21, 2018, Inhaber et al.
(Continued)

*Primary Examiner* — Benjamin J Klein
(74) *Attorney, Agent, or Firm* — Eversheds Sutherland (US) LLP; Christopher C. Bolten; Nicola A. Pisano

(57) ABSTRACT

A fluid management system for moving bodily fluid accumulated due to ascites, pleural effusion or pericardial effusion is provided including an implantable pump coupled to an inflow catheter, an outflow catheter, and optionally an anti-clog catheter. The fluid management system facilitates removal of fluid from a body region, such as the peritoneum, pleural cavity or pericardial sac, where drainage is desired to another body region, such as the urinary bladder or the peritoneal cavity. The system includes clog resistant mechanisms such as clog resistant catheters and/or programmed routines for cycling fluid through inlet catheters in predetermined time intervals and/or responsive to sensed conditions to minimize the risk that inlet catheters become clogged due to, for example, tissue ingrowth and/or solid objects within accumulated fluid.

17 Claims, 8 Drawing Sheets

(51) Int. Cl.
*A61M 5/142* (2006.01)
*A61M 25/00* (2006.01)
*A61M 5/172* (2006.01)
*A61M 5/168* (2006.01)
*A61M 5/14* (2006.01)

(52) U.S. Cl.
CPC ....... *A61M 27/006* (2013.01); *A61M 5/16836* (2013.01); *A61M 5/16854* (2013.01); *A61M 5/172* (2013.01); *A61M 2005/1403* (2013.01); *A61M 2005/16863* (2013.01); *A61M 2025/0019* (2013.01); *A61M 2205/3331* (2013.01); *A61M 2205/3334* (2013.01); *A61M 2205/3523* (2013.01); *A61M 2205/3561* (2013.01)

(58) Field of Classification Search
CPC ........ A61M 27/006; A61M 2025/0019; A61M 2205/3331; A61M 2205/3334
See application file for complete search history.

(56) References Cited

U.S. PATENT DOCUMENTS

| | | |
|---|---|---|
| 3,654,932 A | 4/1972 | Newkirk et al. |
| 3,810,259 A | 5/1974 | Summers |
| 3,910,283 A | 10/1975 | Leveen |
| 4,014,346 A | 3/1977 | Brownlee et al. |
| 4,083,786 A | 4/1978 | Tsuda et al. |
| 4,240,434 A | 12/1980 | Newkirk |
| 4,261,341 A | 4/1981 | Hakim et al. |
| 4,354,933 A | 10/1982 | Lester |
| 4,416,657 A | 11/1983 | Berglund |
| 4,419,094 A | 12/1983 | Patel |
| 4,475,898 A | 10/1984 | Brodner et al. |
| 4,475,899 A | 10/1984 | Muller |
| 4,490,137 A | 12/1984 | Moukheibir |
| 4,553,956 A | 11/1985 | Muller |
| 4,610,625 A | 9/1986 | Bunn |
| 4,610,658 A | 9/1986 | Buchwald et al. |
| 4,615,691 A | 10/1986 | Hakim et al. |
| 4,618,343 A | 10/1986 | Polaschegg |
| 4,632,435 A | 12/1986 | Polyak |
| 4,657,530 A | 4/1987 | Buchwald et al. |
| 4,687,471 A | 8/1987 | Twardowski et al. |
| 4,725,207 A | 2/1988 | Buchwald et al. |
| 4,772,257 A | 9/1988 | Hakim et al. |
| 4,779,614 A | 10/1988 | Moise |
| 4,784,638 A | 11/1988 | Ghajar et al. |
| 4,850,955 A | 7/1989 | Newkirk et al. |
| 4,880,414 A | 11/1989 | Whipple |
| 4,904,236 A | 2/1990 | Redmont et al. |
| 4,963,129 A | 10/1990 | Rusch |
| 4,963,133 A | 10/1990 | Whipple |
| 5,011,472 A | 4/1991 | Aebischer et al. |
| 5,021,048 A | 6/1991 | Buckholtz |
| 5,037,385 A | 8/1991 | O'Byrne |
| 5,057,075 A | 10/1991 | Moncrief et al. |
| 5,071,408 A | 12/1991 | Ahmed et al. |
| 5,078,688 A | 1/1992 | Lobodzinski et al. |
| 5,147,281 A | 9/1992 | Thornton et al. |
| 5,167,615 A | 12/1992 | East et al. |
| 5,180,387 A | 1/1993 | Ghajar et al. |
| 5,254,084 A | 10/1993 | Geary |
| 5,356,386 A | 10/1994 | Goldberg et al. |
| 5,385,541 A | 1/1995 | Kirsch et al. |
| 5,387,188 A | 2/1995 | Watson |
| 5,387,192 A | 2/1995 | Glantz et al. |
| 5,391,143 A | 2/1995 | Kensey |
| 5,395,350 A | 3/1995 | Summers |
| 5,397,354 A | 3/1995 | Wilk et al. |
| 5,472,323 A | 12/1995 | Hirabayashi et al. |
| 5,474,683 A | 12/1995 | Bryant et al. |
| 5,575,770 A | 11/1996 | Melsky et al. |
| 5,589,197 A | 12/1996 | Shockley et al. |
| 5,629,025 A | 5/1997 | Shockley et al. |
| 5,631,025 A | 5/1997 | Shockley et al. |
| 5,637,083 A | 6/1997 | Bertrand et al. |
| 5,725,506 A | 3/1998 | Freeman et al. |
| 5,830,172 A | 11/1998 | Leveen et al. |
| 5,902,336 A | 5/1999 | Mishkin |
| 5,944,684 A | 8/1999 | Roberts et al. |
| 5,947,911 A | 9/1999 | Wong et al. |
| 5,980,478 A | 11/1999 | Gorsuch et al. |
| 5,989,207 A | 11/1999 | Hughes |
| 6,007,511 A | 12/1999 | Prywes |
| 6,017,355 A | 1/2000 | Hessel et al. |
| D420,738 S | 2/2000 | Carter et al. |
| 6,022,333 A | 2/2000 | Kensey |
| 6,132,405 A | 10/2000 | Nilsson et al. |
| 6,132,415 A | 10/2000 | Finch et al. |
| 6,162,238 A | 12/2000 | Kaplan et al. |
| 6,162,487 A | 12/2000 | Darouiche |
| 6,193,684 B1 | 2/2001 | Burbank et al. |
| 6,214,802 B1 | 4/2001 | Nakamura et al. |
| 6,245,039 B1 | 6/2001 | Brugger et al. |
| 6,248,726 B1 | 6/2001 | Alsop et al. |
| 6,254,567 B1 | 7/2001 | Treu et al. |
| 6,264,601 B1 | 7/2001 | Jassawalla et al. |
| 6,264,625 B1 | 7/2001 | Rubenstein et al. |
| 6,417,750 B1 | 7/2002 | Sohn |
| 6,436,087 B1 | 8/2002 | Lewis et al. |
| 6,533,733 B1 | 3/2003 | Ericson et al. |
| 6,554,822 B1 | 4/2003 | Holschneider et al. |
| 6,585,681 B2 | 7/2003 | Brugger et al. |
| 6,613,095 B1 | 9/2003 | Levin |
| 6,656,227 B2 | 12/2003 | Levin |
| 6,689,085 B1 | 2/2004 | Rubenstein et al. |
| 6,814,547 B2 | 11/2004 | Childers et al. |
| 6,827,682 B2 | 12/2004 | Bugge et al. |
| 6,845,267 B2 | 1/2005 | Harrison et al. |
| 6,846,168 B2 | 1/2005 | Davis et al. |
| 6,854,467 B2 | 2/2005 | Boekstegers |
| 6,875,192 B1 | 4/2005 | Saul et al. |
| 6,887,214 B1 | 5/2005 | Levin et al. |
| 6,894,456 B2 | 5/2005 | Tsukamoto et al. |
| 6,911,014 B2 | 6/2005 | Wentling et al. |
| 6,921,378 B2 | 7/2005 | O'Keefe et al. |
| 6,926,691 B2 | 8/2005 | Miethke |
| 6,939,111 B2 | 9/2005 | Huitt et al. |
| 6,945,949 B2 | 9/2005 | Wilk |
| 6,949,080 B2 | 9/2005 | Wolf et al. |
| 6,953,481 B2 | 10/2005 | Phelps et al. |
| 6,955,655 B2 | 10/2005 | Burbank et al. |
| 6,960,179 B2 | 11/2005 | Gura |
| 6,964,652 B2 | 11/2005 | Guiles et al. |
| 6,974,445 B2 | 12/2005 | Stergiopulos |
| 6,976,973 B1 | 12/2005 | Ruddell et al. |
| 6,979,351 B2 | 12/2005 | Forsell et al. |
| 6,981,964 B2 | 1/2006 | Rioux et al. |
| 6,994,700 B2 | 2/2006 | Elkins et al. |
| 7,011,095 B2 | 3/2006 | Wolf et al. |
| 7,017,340 B2 | 3/2006 | Chicky |
| 7,025,739 B2 | 4/2006 | Saul |
| 7,025,742 B2 | 4/2006 | Rubenstein et al. |
| 7,063,679 B2 | 6/2006 | Maguire et al. |
| 7,169,303 B2 | 1/2007 | Sullivan et al. |
| 7,195,608 B2 | 3/2007 | Burnett |
| 7,311,690 B2 | 12/2007 | Burnett |
| 7,335,179 B2 | 2/2008 | Burnett |
| 7,621,886 B2 | 11/2009 | Burnett |
| 7,670,332 B2 | 3/2010 | O'Keefe et al. |
| 7,909,790 B2 | 3/2011 | Burnett |
| 8,012,118 B2 | 9/2011 | Curtin et al. |
| 8,202,248 B2 | 6/2012 | Burnett et al. |
| 8,241,239 B2 | 8/2012 | Solomon et al. |
| 8,394,048 B2 | 3/2013 | Burnett |
| 8,398,577 B2 | 3/2013 | Burnett |
| 8,517,973 B2 | 8/2013 | Burnett |
| 8,585,635 B2 | 11/2013 | Degen et al. |
| 8,641,659 B2 | 2/2014 | Soykan et al. |
| 8,771,221 B2 | 7/2014 | Burnett |
| 8,882,699 B2 | 11/2014 | Burnett |
| 8,961,448 B2 | 2/2015 | Forsell |

(56) References Cited

U.S. PATENT DOCUMENTS

| | | |
|---|---|---|
| 8,992,456 B1 | 3/2015 | Powell |
| 9,039,652 B2 | 5/2015 | Degen et al. |
| 9,138,521 B2 | 9/2015 | Solomon et al. |
| 9,144,660 B2 | 9/2015 | Degen |
| 9,149,613 B2 | 10/2015 | Degen et al. |
| D743,542 S | 11/2015 | Degen |
| D743,543 S | 11/2015 | Degen |
| 9,339,636 B1 | 5/2016 | Khan et al. |
| 9,381,301 B2 | 7/2016 | Lattanzio et al. |
| 9,421,347 B2 | 8/2016 | Burnett |
| 9,577,459 B2 | 2/2017 | Degen et al. |
| 9,675,327 B2 | 6/2017 | Johnson et al. |
| 9,913,968 B2 | 3/2018 | Burnett |
| 9,956,336 B2 | 5/2018 | Degen et al. |
| 2002/0013545 A1 | 1/2002 | Soltanpour et al. |
| 2002/0022793 A1 | 2/2002 | Bertrand et al. |
| 2002/0123715 A1 | 9/2002 | Sorenson et al. |
| 2003/0114787 A1 | 6/2003 | Gura |
| 2003/0163079 A1 | 8/2003 | Burnett |
| 2003/0171710 A1 | 9/2003 | Bassuk et al. |
| 2003/0217962 A1 | 11/2003 | Childers et al. |
| 2003/0220606 A1 | 11/2003 | Busby et al. |
| 2004/0018228 A1 | 1/2004 | Fischell et al. |
| 2004/0049288 A1 | 3/2004 | Levin |
| 2004/0098113 A1 | 5/2004 | Forsell et al. |
| 2004/0126775 A1 | 7/2004 | Altieri et al. |
| 2004/0147871 A1 | 7/2004 | Burnett |
| 2005/0131340 A1 | 6/2005 | Sorenson et al. |
| 2005/0273034 A1 | 12/2005 | Burnett |
| 2006/0010014 A1 | 1/2006 | Brown |
| 2006/0024200 A1 | 2/2006 | Nishikiori et al. |
| 2006/0036208 A1 | 2/2006 | Burnett |
| 2006/0058731 A1* | 3/2006 | Burnett ............... A61M 1/1678 604/29 |
| 2006/0094984 A1 | 5/2006 | Wood et al. |
| 2007/0055197 A1 | 3/2007 | Shakir |
| 2007/0106205 A1 | 5/2007 | Connell et al. |
| 2007/0228071 A1 | 10/2007 | Kamen et al. |
| 2007/0255345 A1 | 11/2007 | Krause |
| 2007/0299317 A1 | 12/2007 | Hoyme et al. |
| 2008/0024294 A1 | 1/2008 | Mazar |
| 2008/0108935 A1 | 5/2008 | Nyhart, Jr. |
| 2008/0154173 A1 | 6/2008 | Burnett |
| 2008/0214983 A1 | 9/2008 | Mauge et al. |
| 2008/0230450 A1 | 9/2008 | Burbank et al. |
| 2009/0069642 A1 | 3/2009 | Gao et al. |
| 2009/0171241 A1 | 7/2009 | Garcia et al. |
| 2009/0198174 A1 | 8/2009 | Childers et al. |
| 2009/0222065 A1 | 9/2009 | Dlugos, Jr. |
| 2009/0275805 A1 | 11/2009 | Lane |
| 2009/0275924 A1 | 11/2009 | Lattanzio et al. |
| 2009/0318844 A1 | 12/2009 | Burnett |
| 2010/0010832 A1 | 1/2010 | Boute et al. |
| 2010/0022902 A1 | 1/2010 | Lee |
| 2010/0114012 A1 | 5/2010 | Sandford et al. |
| 2010/0185225 A1 | 7/2010 | Albrecht |
| 2010/0215375 A1 | 8/2010 | Reams |
| 2010/0234793 A1 | 9/2010 | Dacey, Jr. et al. |
| 2010/0249692 A1 | 9/2010 | Dacey et al. |
| 2010/0312163 A1 | 12/2010 | Forsell |
| 2010/0312164 A1 | 12/2010 | Forsell |
| 2011/0025261 A1 | 2/2011 | Bersenev |
| 2011/0034986 A1 | 2/2011 | Chou et al. |
| 2011/0172545 A1 | 7/2011 | Grudic |
| 2011/0184339 A1 | 7/2011 | Tan |
| 2011/0184340 A1 | 7/2011 | Tan et al. |
| 2012/0041279 A1 | 2/2012 | Freeman |
| 2012/0209085 A1 | 8/2012 | Degen et al. |
| 2012/0209165 A1 | 8/2012 | Degen et al. |
| 2013/0199998 A1 | 8/2013 | Kelly et al. |
| 2013/0211322 A1 | 8/2013 | Degen et al. |
| 2013/0289334 A1 | 10/2013 | Badstibner et al. |
| 2014/0005743 A1 | 1/2014 | Giuffrida |
| 2014/0012180 A1 | 1/2014 | Levin et al. |
| 2014/0066841 A1 | 3/2014 | Degen |
| 2014/0074180 A1 | 3/2014 | Heidman |
| 2014/0275827 A1 | 9/2014 | Gill |
| 2015/0088090 A1* | 3/2015 | Macy, Jr. ............ A61M 25/007 604/500 |
| 2016/0000984 A1 | 1/2016 | Burnett et al. |
| 2016/0022971 A1 | 1/2016 | Degen et al. |
| 2016/0183819 A1 | 6/2016 | Burnett |
| 2017/0079760 A1 | 3/2017 | Newman |
| 2017/0128654 A1 | 5/2017 | Feld |
| 2017/0136221 A1* | 5/2017 | Budgett ............... A61M 27/006 |
| 2018/0060520 A1 | 3/2018 | Degen et al. |
| 2018/0243495 A1 | 8/2018 | Degen et al. |
| 2018/0344917 A1 | 12/2018 | Inhaber et al. |

FOREIGN PATENT DOCUMENTS

| | | |
|---|---|---|
| EP | 0 366 389 A2 | 5/1990 |
| EP | 0 980 685 A2 | 2/2000 |
| EP | 1 362 605 A1 | 11/2003 |
| EP | 1 517 718 B1 | 3/2005 |
| EP | 1 539 294 B1 | 6/2005 |
| EP | 2 244 667 A1 | 11/2010 |
| EP | 2 676 638 B1 | 12/2013 |
| GB | 2 350 794 A | 12/2000 |
| JP | H04-327857 | 11/1992 |
| WO | WO-97/41799 A1 | 11/1997 |
| WO | WO-98/16171 A1 | 4/1998 |
| WO | WO-02/07596 A1 | 1/2002 |
| WO | WO-03/072166 A1 | 9/2003 |
| WO | WO-2004/105730 A1 | 12/2004 |
| WO | WO-2005/018708 A1 | 3/2005 |
| WO | WO-2006/023589 A2 | 3/2006 |
| WO | WO-2009/096854 A1 | 8/2009 |
| WO | WO-2012/112664 A1 | 8/2012 |
| WO | WO-2013/122580 A1 | 8/2013 |
| WO | WO-2013/166038 A2 | 11/2013 |
| WO | WO-2014/140277 A1 | 9/2014 |
| WO | WO-2015/108782 A1 | 7/2015 |
| WO | WO-2018/037359 A1 | 3/2018 |

OTHER PUBLICATIONS

Costanzo et al., "Early Ultrafiltration in Patients with Decompensated Heart Failure and Diuretic Resistance," J. Am. Coll. Cardiol., (2005), vol. 46(11):2047-2051.

Houlberg et al., "Terminal Right Heart Failure Due to Complex Congenital Cardiac Disease Successfully Managed by Home Peritoneal Drainage," Cardiol. Young, 13(6):568-70 (2003).

International Search Report dated Sep. 16, 2008 in Int'l PCT Appl. Serial No. PCT/US2005/029305.

International Search Report & Written Opinion dated Mar. 18, 2013 in Int'l PCT Appl. Serial No. PCT/US2012/025188.

Partial International Search dated Dec. 8, 2017 in Int'l PCT Patent Appl. No. PCT/IB17/55093.

International Search Report and Written Opinion dated Feb. 2, 2018 in Int'l PCT Patent Appl. No. PCT/IB2017/055093.

Medtronic Reveal LinqTM LNQ11, Insertable Cardiac Monitor, Clinician Manual, 98 pages (2015).

Ortiz et al., "Long-Term Automated Peritoneal Dialysis in Patients with Refractory Congestive Heart Failure," Advances in Peritoneal Dialysis, (2003), vol. 19:77-80.

www.medtronic.com/us-en/patients/treatments-therapies/fainting-heart-monitor/reveal-linq-icm.html (May 2017) (Accessed Nov. 27, 2017).

International Search Report & Written Opinion dated Jan. 4, 2018 in Int'l PCT Patent Appl. Serial No. PCT/IB2017/055092.

Doty, et al., Effect of Increased Renal Venous Pressure on Renal Function, J. Trauma., 47(6):1000-3 (1999).

Francois, et al., Peritoneal Dialysis for Chronic Congestive Heart Failure, Blood Purif., 40(1):45-52 (2015).

Hecking, et al., Sodium Setpoint and Sodium Gradient: Influence on Plasma Sodium Change and Weight Gain, Am J. Nephrol, 33(1):39-48 (2011).

Kenny, Intra-Abdominal Pressure and Renal Function: The Venous Side of the Road, PulmCCM, Critical Carer, GI and Nutrition, Jul.

(56) References Cited

OTHER PUBLICATIONS 14, 2016, accessed on line on Mar. 27, 2017 at http://pulmccm.org/main/2016/critical-care-review/intra-abdominal-pressure-renal-function/.

McCausland, et al., Dialysate Sodium, Serum Sodium and Mortality in Maintenance Hemodialysis, 27(4):1613-1618 (2012).

Munoz Mendoza, et al., Dialysate sodium and sodium gradient in maintenance hemodialysis: a neglected sodium restriction approach? Nephrol Dial Transplant, 26(4):1281-1287 (2011).

Nakayama, et al., Clinical Effect of Low Na Concentration Dialysate (120mEq/L) for CAPD Patients, Abstracts of the XIII Annual CAPD Conference, Peritoneal Dialysis International, vol. 13, Supplement 1, 1993.

Puttagunta, et al., Peritoneal Dialysis for Heart Failure, Peritoneal Dialysis International, 35(6):645-649 (2015.

Rosenblit et al., "Peritoneal-Urinary Drainage for Treatment of Refractory Ascites: A Pilot Study," J. of Vascular & Interventional Radiology, 9(6):998-1005 (1998).

Ruhi, et al., Use of Peritoneal Ultrafiltration in the Elderly Refractory Congestive Heart Failure Patients, Int. Urol. and Nephrol., 44(3):963-969 (2012).

Zepeda-Orozco, et al., Dialysis Disequilibrium Syndrome, Pediatr. Nephrol, 27:2205-2211 (2012).

Extended European Search Report dated Sep. 18, 2019 in EP Patent Appl. Serial No. 19172235.4 (0831 EP).

U.S. Appl. No. 13/397,509 / U.S. Pat. No. 9,149,613, filed Feb. 15, 2012 / Oct. 6, 2015.

U.S. Appl. No. 13/397,523 / U.S. Pat. No. 9,039,652, filed Feb. 15, 2012 / May 26, 2015.

U.S. Appl. No. 14/155,079, filed Jan. 14, 2014.

U.S. Appl. No. 14/874,187, filed Oct. 2, 2015.

* cited by examiner

IMPLANTABLE FLUID MANAGEMENT SYSTEM HAVING CLOG RESISTANT CATHETERS, AND METHODS OF USING SAME

I. FIELD OF THE INVENTION

This application relates to apparatus and methods for minimizing catheter clogging in the treatment of intracorporeal fluid accumulations, such as ascites, pleural effusion, and pericardial effusion.

II. BACKGROUND OF THE INVENTION

There are a variety of conditions which result in pathologic chronic collection of bodily fluids within the peritoneum, pleura or pericardial sac. Chronic ascites, pleural effusion and pericardial effusion are conditions in which chronic fluid collections persist and result in increased morbidity and mortality.

These foregoing conditions currently are treated typically by one of three methods: 1) external drainage, which poses a risk of infection and long-term requirement for multiple punctures, 2) drainage to another body cavity, or 3) treatment with drugs. In pleural effusion, excess fluid arising from an underlying pathology, such as lung cancer, breast cancer or lymphoma, accumulates in the pleural cavity. If left untreated, the fluid accumulation may interfere with proper lung function, significantly increasing morbidity and mortality. Depending upon the underlying cause of the pleural effusion, treatment may consist of drug therapy, thoracentesis, in which a needle is periodically inserted through the chest and into the pleural cavity to drain the fluid accumulations, or installation of an intercostal drain, in which one end of a pigtail catheter is inserted into the pleural cavity and the fluid is drained to an external canister. Although a relatively simple procedure, placement of an intercostal drain is associated with a relatively high rate of major complications, including hemorrhage and infection. Repeated effusions also may be treated by pleurodesis, in which two pleural surfaces are attached to one another so that no fluid can accumulate between them. However, this procedure requires a lengthy hospital stay and is reported to be associated with the onset of adult respiratory distress syndrome, a potentially life-threatening complication.

In pericardial effusion, fluid accumulates in the pericardial sac and may lead to increased intrapercardial pressure and reduced cardiac output. Where the fluid accumulation interferes with proper heart function, pericardiocentesis may be performed, in which the fluid is drained to an external site through a needle or catheter inserted through the chest wall and into the pericardial sac. For chronic cases, the treatment of choice is formation of a pericardial window. In this highly invasive procedure, a section of the pericardial sac is removed to create a fistula that permits fluid to drain to the abdomen. Although this procedure is usually well tolerated by patients, the pericardial window may close, requiring re-operation.

Ascites is a highly debilitating complication associated with many medical conditions including liver failure, congestive heart failure and certain cancers. Untreated ascites can result in respiratory compromise, compression of the inferior vena cava (a vital blood vessel) and spontaneous bacterial peritonitis (a life-threatening condition). Conventional treatment for ascites includes a regime of drugs and dietary restriction, and for chronic cases, repeated surgical interventions.

Previously known attempts to treat ascites have included indwelling catheters including external ports, squeeze-bulbs and magnetically-driven reciprocating pumps to transfer ascites from the peritoneal cavity into the venous vasculature, through an external port, or into the bladder. For example, U.S. Pat. No. 4,240,434 to Newkirk and U.S. Pat. No. 4,657,530 to Buchwald each describes a squeezable tube-type ascites shunt having an inlet end configured to the placed in the peritoneal cavity and an outlet end configured to be placed in a vein. Rosenblit et al., in an article entitled "Peritoneal-Urinary Drainage for Treatment of Refractory Ascites: A Pilot Study," J. Vascular & Interv. Radiology, 9(6):998-1005 (November/December 1998) describes a similar squeeze-bulb system having an outlet disposed in the bladder. U.S. Pat. No. 4,610,658 to Buchwald et al. describes an implantable pump for treating ascites that includes a magnetically-driven pump to transfer fluid from the peritoneal cavity to the vasculature system. Such previously known devices suffer from a variety of drawbacks, including fibrous encapsulation, frequent clogging and infection. Such devices provided little improvement over periodic paracenteses, and resulted in increased rates of infection, re-operation or other complications if left in place for any length of time. Moreover, a key drawback of such previously-known systems is the requirement that the patient must repeatedly locate and manually actuate the pumping mechanism on a daily basis. Such activity may be difficult for patients, especially the elderly and obese, and further complicated by an ascites-distended abdomen. Consequently, the difficulty of manipulating such previously-known systems promotes patient non-compliance, in turn leading to clogging and infection.

Such clogging in previously-known systems was especially problematic at an inlet catheter, if provided. An inlet catheter implanted in the peritoneal cavity for treatment of ascites is prone to clogging due to the viscous properties of fluid in the cavity. In addition, inlet catheters are susceptible to clogging due to tissue ingrowth and solid objects within the accumulated fluid.

In view of the above-noted drawbacks of previously-known systems, it would be desirable to provide methods and apparatus for treating ascites and other intracorporeal fluid accumulations using implantable devices that are resistant to clogging.

III. SUMMARY OF THE INVENTION

The present invention overcomes the drawbacks of previously-known systems by providing a fluid management system that automatically and autonomously moves fluid accumulations using clog resistant mechanisms including clog resistant catheters and programmed routines to run "anti-clog cycles" to cycle fluid out inflow catheter(s) in predetermined time intervals or responsive to sensed conditions.

The fluid management system preferably includes a first catheter, an optional second catheter, a third catheter, and an implantable housing containing a pump and a microcontroller. The first catheter has an inlet end adapted to be positioned within a first cavity, e.g., peritoneal cavity, pleural cavity, or pericardial cavity, and an outlet end. The second catheter has an inlet end adapted to be positioned within a body cavity, e.g., the first cavity, and an outlet end. The third catheter has an inlet end and an outlet end adapted to be positioned in a second cavity, e.g., bladder or pericardial cavity. The implantable housing may be coupled to the outlet end of the first catheter, the outlet end of the second catheter and the inlet end of the third catheter. The system may include a first valve operatively associated with the implantable housing and movable in response to the microcontroller. The first valve may be a duckbill valve or a mechanical valve such as a monostable valve or a bistable valve.

A non-transitory programmed routine is stored in memory associated with the microcontroller. The programmed routine may be configured to selectably actuate the pump to move fluid in a first direction through the first catheter toward the outlet end of the third catheter during a first time interval, and periodically to actuate the first valve to place the outlet end of the second catheter in fluid communication with the outlet end of the first catheter and to actuate the pump to move fluid in a second direction through the first catheter, opposite to the first direction, and out the inlet end of the first catheter to reduce potential clogging in the first catheter. The programmed routine may be configured to open or close the first valve during the first time interval when the pump is actuated to move fluid in the first direction through the first catheter toward the outlet end of the third catheter.

The system may include a second valve operatively coupled to the third catheter and configured to prevent reverse flow from the third catheter to the first catheter or the second catheter. The second and third catheters may be separate or coupled together to create a Y-shaped catheter.

The implantable housing may include a plurality of sensors for sensing physiological conditions within the body including a source pressure sensor configured to measure pressure of fluid within the first catheter, a sink pressure sensor configured to measure pressure of fluid in the third catheter, and/or a pressure sensor configured to measure pressure of fluid within the second catheter.

The pump in the implantable housing may include a gear pump coupled to an electric motor disposed within the implantable housing, wherein, in the first direction, the gear pump rotates in a forward direction and, in the second direction, the gear pump rotates in a reverse direction.

The present disclosure provides variations of inflow catheters with anti-clogging mechanisms suitable for use with the fluid management system. The first catheter may have a plurality of through-holes configured to permit fluid in the first cavity to enter a lumen of the first catheter. A first portion of the holes may be sized with a first diameter and a second portion of the holes may be sized with a second diameter, smaller than the first diameter. Preferably, the second portion of the holes is disposed proximal to the first portion along the first catheter. A mesh sleeve may be disposed on an outer surface of the first catheter and configured to permit fluid to flow therethrough and into the holes and to minimize solid objects from flowing therethrough. The holes may have a truncated cone shape such that a smaller diameter portion of the truncated cone is disposed at an outer surface of the first catheter and a larger diameter portion of the truncated cone is disposed at an inner surface of the first catheter. The first catheter may include more than one lumen such that a first portion of the holes permits fluid to flow into the lumen and a second portion of the holes permits fluid to flow into a second lumen, for example.

In one embodiment, the system further includes a fourth catheter having an inlet end adapted to be positioned within a third cavity, e.g., peritoneal cavity, pleural cavity, or pericardial cavity, different from the first cavity, and an outlet end coupled to the implantable housing. Such an embodiment permits interchangeable or simultaneous drainage of the first and third cavities to the second cavity and permits periodic flushing of the first and fourth catheters using the second catheter.

In accordance with one aspect of the present invention, a method for reducing clogging in a fluid management system is described. The method may include providing a first catheter having an inlet end and an outlet end, a second catheter having an inlet end and an outlet end, a third catheter having an inlet end and an outlet end, and an implantable housing containing a pump, the housing coupled to the outlet end of the first catheter, the outlet end of the second catheter, and the inlet end of the third catheter; selectably actuating the pump to move bodily fluid in a first cavity in a first direction through the first catheter and out the outlet end of the third catheter in a second body cavity during a first time interval; and periodically actuating the pump to move fluid in a second direction through the first catheter, opposite to the first direction, and out the inlet end of the first catheter to reduce potential clogging in the first catheter.

IV. BRIEF DESCRIPTION OF THE DRAWINGS

V. DETAILED DESCRIPTION OF THE INVENTION

The fluid management system of the present invention comprises devices for facilitating removal of fluid from a body region, such as the peritoneum, pleural cavity or pericardial sac, where drainage is desired. The devices disclosed herein may be utilized for drainage of chronic excess fluid accumulation from one body cavity to a second body cavity, preferably the urinary bladder or the peritoneal cavity. To minimize the risk that inlet catheters disposed in a body cavity become clogged due to, for example, tissue ingrowth and/or solid objects within accumulated fluid, the system preferably includes clog resistant mechanisms such as clog resistant catheters and programmed routines for cycling fluid through inlet catheters in predetermined time intervals and/or responsive to sensed conditions.

Figure 1:
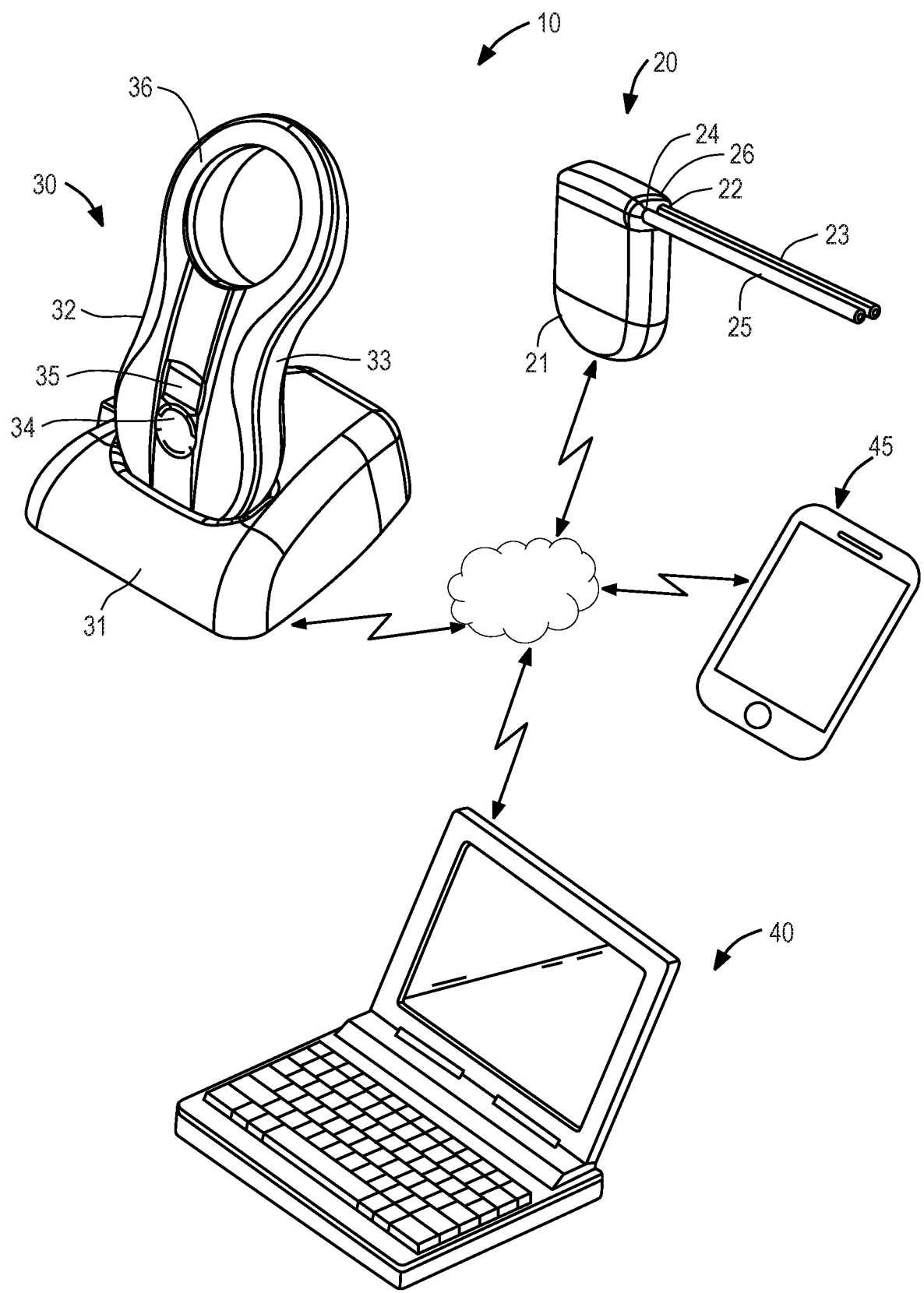
FIG. 1 is a perspective view of the components of an exemplary fluid management system constructed in accordance with the principles of the present invention.

Referring to FIG. 1, an exemplary embodiment of a system suitable for use with the clog resistant mechanisms of the present invention is described. System 10 is similar to that described in U.S. Pat. No. 9,149,613 to Degen et al., assigned to the assignee of the present application, the entirety of which is incorporated herein by reference. System 10 illustratively comprises implantable device 20, charging and communication system 30, monitoring and control system 40, and mobile device 45. Each of charging and communication system 30, monitoring and control system 40, and mobile device 45 may communicate with one another and with implantable device 20.

As will be understood, implantable device 20 is configured to be implanted subcutaneously within a human body, while charging and communication charging system 30 is configured to be periodically placed over the skin in the vicinity of the implantable device to charge and communicate with the implantable device. Implantable device 20 may connect with charging and communication system 30, monitoring and control system 40, and/or mobile device 45 to provide real time monitoring data and operating parameters.

Implantable device 20 illustratively comprises an electromechanical pump having housing 21 configured for subcutaneous implantation. In one embodiment suitable for treating ascites, implantable device 20 includes an electrically-driven mechanical gear pump having inlet port 22 coupled to inlet catheter 23 and outlet port 24 coupled to outlet catheter 25. The gear pump is configured to rotate in a forward direction and in a reverse direction. Inlet catheter 23 comprises a tube having a first end configured to be coupled to pump inlet 23 and a second end adapted to be positioned in a patient's peritoneal cavity. Outlet catheter 25 comprises a tube having a first end configured to be coupled to pump outlet 24 and a second end adapted to be inserted through the wall of, and fixed within, a patient's bladder. Inlet catheter 23 and outlet catheter 25 are coupled to pump housing 21 using connector 26 configured to reduce the risk of improper installation and inadvertent disconnection, and may in addition include distinct cross-sections that reduce the risk of improper installation. As will be readily understood by one of ordinary skill in the art, while implantable device 20 is illustratively coupled to two catheters, implantable device 20 may be coupled to additional catheters, as is described in detail below. Implantable device 20 preferably further comprises a wireless communication chip (e.g., compatible with cellular, WLAN, and/or BLUETOOTH™ standards) for communicating with charging and communication system 30, monitoring and control system 40, and/or mobile device 45.

Charging and communication system 30 is external to the patient and illustratively comprises base 31 and handpiece 32. Handpiece 32 may house, in housing 33, a controller, a radio transceiver, an inductive charging circuit, a battery, a quality-of-charging indicator and a display, and is removably coupled to base 31 to recharge its battery. Base 31 may contain a transformer and circuitry for converting conventional 120V or 220V power service to a suitable DC current to charge handpiece 32 when coupled to base 31. Alternatively, handpiece 32 may include such circuitry and a detachable power cord that permits the handpiece to be directly plugged into a conventional 120V or 220V wall socket to charge the battery. Handpiece 32 additionally has multi-function button 34, display 35, a plurality of light emitting diodes (LEDs, not shown), and inductive coil portion 36. Charging and communication system 30 may include communication circuitry and may allow for wired or wireless transfer of information to implantable device 20, monitoring and control system 40, mobile device 45 and remote servers.

Monitoring and control system 40 is preferably installed on a dedicated computer. During patient visits, charging and communication system 30 may be coupled, either wirelessly or using a cable, to monitoring and control system 40 to download for review data stored on implantable device 20, or to adjust the operational parameters of implantable device 20. Alternatively, the dedicated computer may connect wirelessly to implantable device 20 allowing monitoring and control system 40 to directly download data stored on implantable device 20 and adjust the operational parameters without the use of charging and communication system 30. Preferably, a physician may adjust timing intervals for running anti-clogging cycles and monitor data stored on implantable device 20 including data indicative of clogging at an inlet catheter. Monitoring and control system 40 also may be configured to upload and store data retrieved to a remote server for later access by the physician or charging and communications system 30.

Mobile device 45 may be any mobile device (e.g., smartphone, tablet, smartwatch, laptop, dedicated custom device, etc.) of the user/patient/caregiver and is illustratively a smartphone. Mobile device 45 may wirelessly connect directly to the implantable device and receive data from implantable device via, for example, SMS text, email, and/or voicemail. When the implantable device 20 experiences an abnormality, malfunction or certain parameters are above or below a preprogrammed threshold(s), implantable device 20 may send an automated message or alarm to mobile device 45. For example, implantable device 20 may instantly message mobile device 45 upon detection that a parameter (e.g., temperature, pressure, and/or humidity) sensed by a sensor(s) of implantable device 20 is outside a predetermined range stored in memory of implantable device 20. An alert also may be sent to the physician via monitoring and control system 40. Alternatively, should a physician observe an abnormality when using monitoring and control system 40, the physician may send an alert from monitoring and control system 40 directly to mobile device 45. Implantable device 20 also may seek input directly from the patient via the mobile device 45. For example, where implantable device 20 detects a clogged catheter, implantable device 20 may alert mobile device 45 of the problem and seek authority to alleviate the clogged catheter by activating an anti-clog catheter discussed in more detail below.

In the configuration where charging and communication system 30 is in wireless communication with implantable device 20 and further in wired or wireless communication with one or more remote servers, the information communicated from implantable device 20 to charging and communication system 30 may then be communicated to one or more remote servers. From the one or more remote servers the information may be shared with a remote analyst. In this way the remote analyst may access the information communicated from implantable device 20 and analyze the information. For example, the data analyst may look for trends or anomalies in the data and may compare the data to data received from other individual's implantable devices and/or to data from other implantable devices in the same patient. The data also may be compared to predetermined or calculated thresholds. The analyst may generate analysis, reports and/or warnings and communicate the analysis, reports and/or warnings to the one or more remote servers for retrieval by other devices in the fluid management system such as charging and communication system 30, monitoring and control device 40 and/or mobile device 45. Alternatively, or in addition to, the analyst may communicate the analysis, reports and/or warnings directly to charging and communication system 30, monitoring and control device 40 and/or mobile device 45 using a wired or wireless connection. The analysis, reports and/or warnings may also be communicated to a physician via phone or email.

Figure 2:
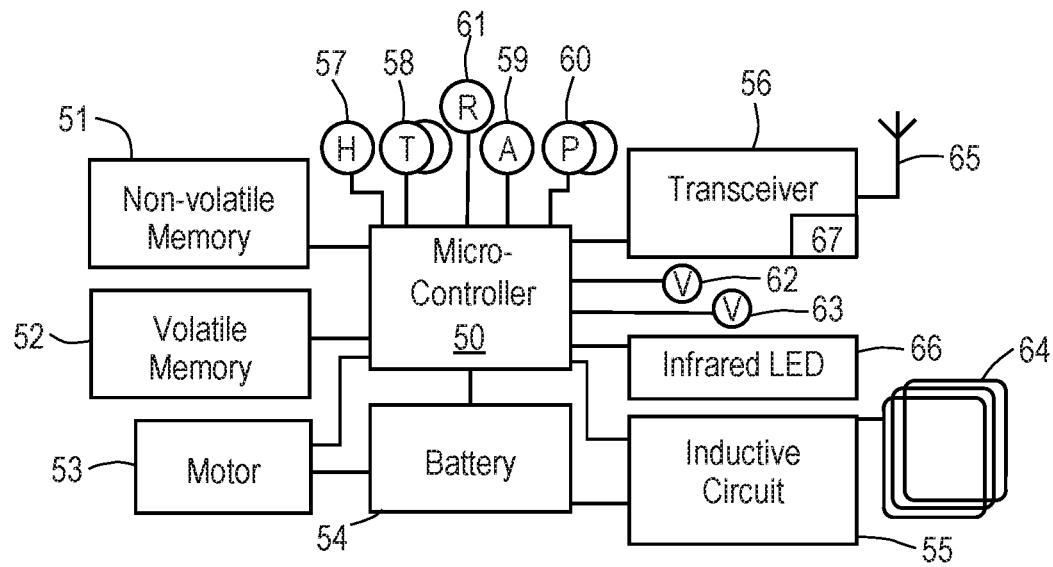
FIG. 2 is a schematic diagram of the electronic components of an exemplary embodiment of the implantable device of the present invention.
Figure 3:
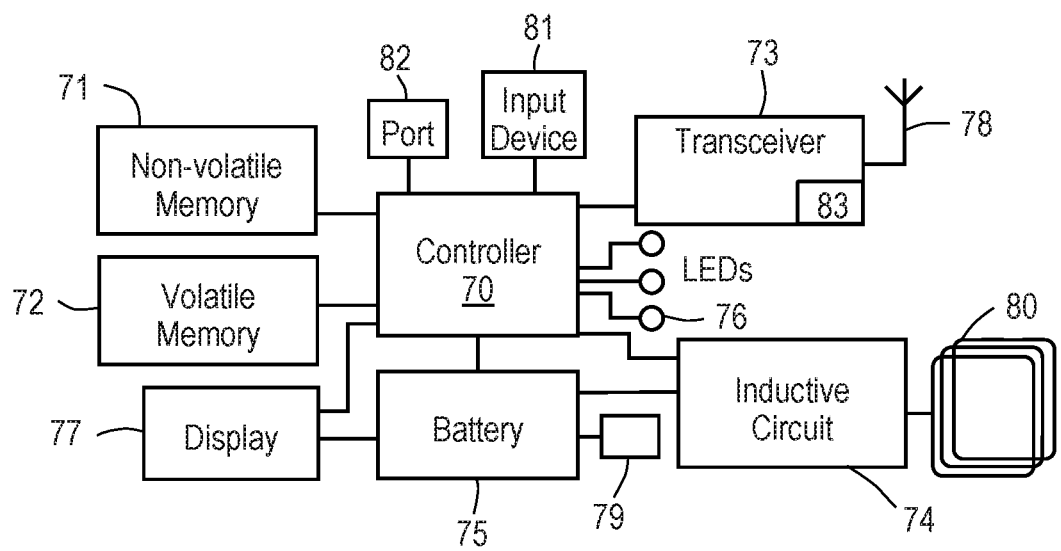
FIG. 3 is a schematic diagram of the electronic components of an exemplary embodiment of the charging and communication system of the present invention.

Referring now to FIGS. 2 and 3, schematic diagrams of exemplary functional blocks of implantable device 20 and charging and communication system 30, respectively, are described.

In particular, in FIG. 2, implantable device 20 includes control circuitry, illustratively microcontroller 50 coupled to nonvolatile memory 51, such as flash memory or electrically erasable programmable read only memory, and volatile memory 52 via data buses. Microcontroller 50 is electrically coupled to electric motor 53, battery 54, inductive circuit 55, radio transceiver 56, a plurality of sensors, including humidity sensor 57, a plurality of temperature sensors 58, accelerometer 59, a plurality of pressure sensors 60, and respiratory rate sensor 61, and a plurality of valves 62, 63. Inductive circuit 55 is electrically coupled to coil 64 to receive energy transmitted from charging and communication system 30. All of the components depicted in FIG. 2 are contained within a low volume sealed biocompatible housing, as shown in FIG. 1. Implantable device 20 optionally may include infrared LED 66 for emitting an infrared signal that is detected by an infrared sensor in handpiece 32 to assist in positioning handpiece 32 to optimize magnetic coupling between the respective inductive coils. Transceiver 56 incorporates wireless communication chip 67 and is coupled to antenna 65. Wireless communication chip 67 may be a communication chip conforming to cellular standards such as GSM, LTE, CDMA, BLUETOOTH™, ZigBee, and/or any IEEE 802.11 wireless standard such as Wi-Fi or Wi-Fi Direct. Wireless communication chip 67 may conform to the cellular standard providing for SMS text and voice message capability. Implantable device 20 is configured to communicate with charging and communication system 30 to transmit information relating to the functioning of implantable device 20 and/or physiological parameters sensed by the sensor(s) of implantable device 20. Wireless communication chip 67 also may communicate directly to monitoring and control system 40 and/or to patient's mobile device 45. Implantable device 20 may automatically connect to local Wi-Fi in the physician's office or alternatively make a direct connection to monitoring and control system 40 and/or mobile device 45 via Wi-Fi Direct. Should wireless communication chip 67 conform to the cellular standard, implantable device 20 may email such information to monitoring and control system 40 and/or mobile device 45 and also may SMS text or voice message mobile device 45. It is further understood that wireless communication chip 67 may conform to more than one communication standard. For example, wireless communication chip 67 may have both Wi-Fi and cellular functionality.

Microcontroller 50 executes firmware stored in nonvolatile memory 51 which controls operation of motor 53 and valves 62, 63 responsive to signals generated by motor 53, sensors 57-61 and commands received from transceiver 56. Preferably, nonvolatile memory 51 stores a non-transitory programmed routine configured to selectably actuate pump motor 53 and valves 62, 63 to unclog a catheter or minimize risk of catheter clogging. In one embodiment, the routine directs the pump to move fluid in a forward direction from the inlet catheter to the outlet catheter and then to move fluid in the reverse direction from an additional catheter out the inlet catheter to reduce potential clogging in the inlet catheter. The routine may direct the pump to in the reverse direction responsive to a predetermined passage of time (e.g., once a day), a predetermined number of pumping cycles (e.g., once every 10 cycles), and/or responsive to a condition indicative of clogging sensed by sensors 57-61.

Microcontroller 50 also controls reception and transmission of messages via transceiver 56 and operation of inductive circuit 55 to charge battery 54. Such messages may include adjustments to the anti-clogging routine described above. Inductive circuit 55 is configured to recharge battery 54 of the implantable device when exposed to a magnetic field supplied to coil 64 by a corresponding inductive circuit within handpiece 32 of charging and communication system 30. In addition, inductive circuit 55 optionally may be configured not only to recharge battery 54, but to directly provide energy to motor 53 in a "boost" mode or jog/shake mode to unblock the pump. Additional operational details relating to the components of implantable device 20 are available in the above-incorporated patent.

Referring now to FIG. 3, handpiece 32 and/or base 31 of charging and communication system 30 contains controller 70, illustratively the processor of a microcontroller unit coupled to nonvolatile memory 71 (e.g., either EEPROM or flash memory), volatile memory 72, radio transceiver 73, inductive circuit 74, battery 75, indicator 76 and display 77. Controller 70, memories 71 and 72, and radio transceiver 73 may be incorporated into a single microcontroller unit, such as the MPS430 family of microprocessors, available from Texas Instruments Incorporated, Dallas, Tex. Transceiver 73 is coupled to antenna 78 for sending and receiving information to and from implantable device 20. Transceiver 73 of charging and communication system 30 may include wireless communication chip 83, that may conform to the cellular, BLUETOOTH™, ZigBee and/or IEEE 802.11 wireless standards, thereby enabling charging and communication system 30 to communicate wirelessly with implantable device 20, monitoring and control system 40, and/or mobile device 45. The communication circuitry of charging and communication system 30 also may allow for wireless transfer of information (e.g., data associated with the functionality of implantable device 20 and/or physiological parameters sensed by implantable device 20) received from implantable device 20 to remote servers. It is further understood that wireless communication chip 83 may be compatible with more than one type of communication standard. Battery 75 is coupled to connector 79 that removably couples with a connector in base 31 to recharge the battery. Inductive circuit 74 is coupled to coil 80. Input device 81, preferably a multi-function button, also is coupled to controller 70 to enable a patient to input a number of commands. Indicator 76 illustratively comprises a plurality of LEDs that illuminate to indicate the quality of charge coupling achieved between the handpiece and implantable device, and therefore assist in optimizing the positioning of handpiece 32 relative to the implantable device during recharging.

Controller 70 executes firmware stored in nonvolatile memory 71 that controls communications and charging of the implantable device. Controller 70 preferably is configured to transfer and store data, such as event logs, uploaded to handpiece 32 from the implantable device, for download and review via port 82 on monitoring and control software 40 during physician office visits. Controller 70 also may include firmware for transmitting commands input using input device 81 to the implantable device, and monitoring operation of the implantable device during execution of such commands, for example, during the anti-clogging routine to clear a blockage. In addition, controller 70 controls and monitors various power operations of handpiece 32, including operation of inductive circuit 74 during recharging of the implantable device, displaying the state of charge of battery 75, and controlling charging and display of state of charge information for battery 54.

Inductive circuit 74 is coupled to coil 80, and is configured to inductively couple with coil 64 of the implantable device to recharge battery 54 of the implantable device. Energy transfer is accomplished via electromagnetic coupling of coil 80 with coil 64 in the implantable device. As will be appreciated by one of ordinary skill, an alternating current is delivered through coil 80, which causes an electromagnetic field to be established around coil 80, which induces an alternating current in coil 64.

Figure 4A:
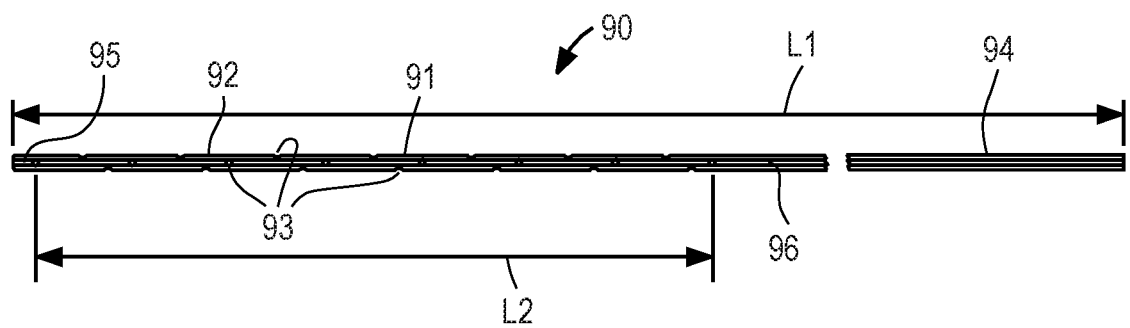
FIGS. 4A and 4B are side views of exemplary embodiments of inflow catheters suitable for use with the system of the present invention.

Referring now to FIG. 4A, exemplary inflow catheter 90 constructed in accordance with the principles of the present invention is described. Inflow catheter 90 may be configured for use in the peritoneal cavity (and thus correspond to peritoneal catheter 23 of FIG. 1) or pleural or pericardial cavity, and preferably comprises tube 91 of medical-grade silicone including inlet end 92 having a plurality of through-wall holes 93 and outlet end 94. When configured for placement in the peritoneal cavity, inflow catheter preferably has length L1 of about 40 cm, with holes 93 extending over length L2 of about 24 cm from inlet end 92. Holes 93 preferably are arranged circumferentially offset by about 90° and longitudinally offset between about 8 mm to 10 mm. In one preferred embodiment, 28 holes 93 are arranged in four rows of 7 holes each, extend only through one wall of the inflow catheter at each location, and have a size of between 2.0 to 2.5 mm. Inflow catheter 90 preferably includes solid silicone plug 95 that fills distal end of the lumen for a distance of about 7-10 mm to reduce tissue ingrowth, and radiopaque strip 96 disposed on, or embedded within, the catheter that extends the entire length of the catheter, that renders the catheter visible in fluoroscopic or X-ray images. Inflow catheter 90 may also include a polyester cuff in the region away from holes 93, to promote adhesion of the catheter to the surrounding tissue, thereby anchoring it in place.

Alternatively, inlet end 92 may include a portion having an enlarged diameter, as disclosed in U.S. Pat. No. 4,657,530, or a reservoir as disclosed in FIGS. 9 to 16 of U.S. Patent Application Publication US 2009/0318844, the entire contents of both of which are incorporated herein by reference, to further reduce the risk of clogging. Inlet end 92 also may terminate in a duck-bill valve, as shown for example in U.S. Pat. No. 4,240,434, thereby permitting the catheter to be cleaned in situ by disconnecting the outlet end of the catheter from implantable device 20 and extending a rod from the outlet end of catheter 90 through the duckbill valve at the inlet end.

Inlet end 92 also may include a polyester cuff to promote adhesion of the catheter to an adjacent tissue wall, thereby ensuring that the inlet end of the catheter remains in position. Outlet end 94 also may include a connector for securing the outlet end of the inflow catheter to implantable device 20. In one preferred embodiment, the distal end of the inflow catheter, up to the ingrowth cuff, may be configured to pass through a conventional 16 F peel-away sheath. In addition, the length of the inflow catheter may be selected to ensure that it lies along the bottom of the body cavity, and is sufficiently resistant to torsional motion so as not to become twisted or kinked during or after implantation.

Figure 4B:
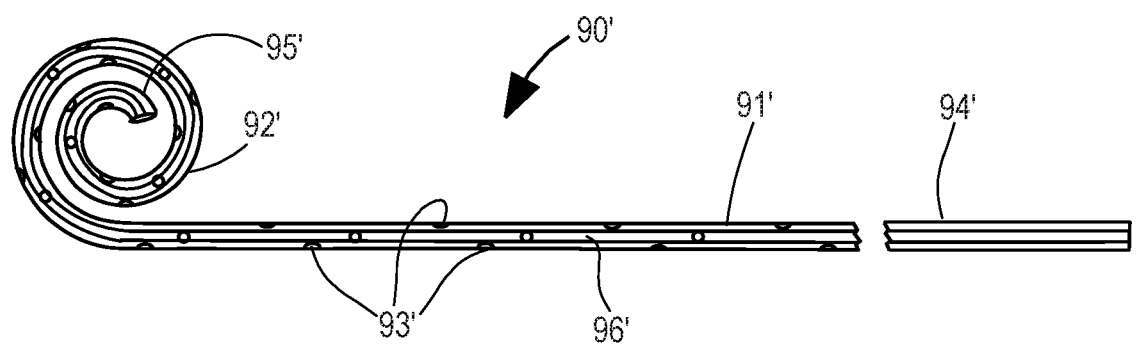

Referring now to FIG. 4B, inlet end 92' of inflow catheter 90' may have a spiral configuration (e.g., "pigtail" shape) to reduce clogging of the catheter. Like inflow catheter 90 of FIG. 4A, inflow catheter 90' preferably comprises tube 91' of medical-grade silicone including inlet end 92' having a plurality of through-wall holes 93' and outlet end 94'. When configured for placement in the peritoneal cavity, inflow catheter has a length with holes 93' extending over a shorter length from inlet end 92'. Holes 93' preferably are arranged circumferentially offset by about 90° and longitudinally offset between about 8 mm to 10 mm. In one preferred embodiment, holes 93' extend only through one wall of the inflow catheter at each location, and have a size of between 2.0 to 2.5 mm. Inflow catheter 90' preferably includes solid silicone plug 95' that fills distal end of the lumen for a distance of about 7-10 mm to reduce tissue ingrowth, and radiopaque strip 96' disposed on, or embedded within, the catheter that extends the entire length of the catheter, that renders the catheter visible in fluoroscopic or X-ray images. Inflow catheter 90' may be implanted using a minimally invasive technique in which the spiral structure is passed through the patient's body in the straightened position and then returned to the coiled shape shown in FIG. 4B upon reaching the appropriate cavity (e.g., peritoneal cavity, pleural cavity, pericardial cavity). Inflow catheter 90' also may include a polyester cuff in the region away from holes 93', to promote adhesion of the catheter to the surrounding tissue, thereby anchoring it in place. Spiral structure may reduce the risk that inflow catheter 90' accidentally will be pulled out of the cavity before the surrounding tissue heals sufficiently to incorporate the polyester cuff.

In one embodiment, the inflow catheter may be shaped, e.g., Y-shaped, to include a plurality of inflow segments to permit inflow from more than one body cavity, as described further below. For example, an inlet end of one segment may be positioned in the peritoneal cavity and the inlet end of another segment may be positioned in the pleural cavity or the pericardial cavity. In an alternative embodiment, more than one inflow catheter may be coupled to implantable device 20 to permit inflow from more than one body cavity. For example, an inlet end of a first inflow catheter may be positioned in the peritoneal cavity and an inlet end of second inflow catheter may be positioned in the pleural cavity or the pericardial cavity. One or more valves may be coupled to the multi-inlet catheter, or the multiple inflow catheters, such that fluid may be pumped from exclusively one cavity or from more than one cavity responsive to commands transmitted by the processor of the microcontroller of implantable device 20 to the valve(s). In yet another alternative embodiment, more than one catheter may be positioned in a single body cavity. For example, an inlet end of a first inflow catheter may be positioned in the peritoneal cavity and an inlet end of a second inflow catheter may be positioned in a different area within the peritoneal cavity.

FIGS. 5-8 are sectional views of portions of different variations of the inlet end of inflow catheter 90 with anti-clogging mechanisms suitable for use with system 10.

Figure 5:
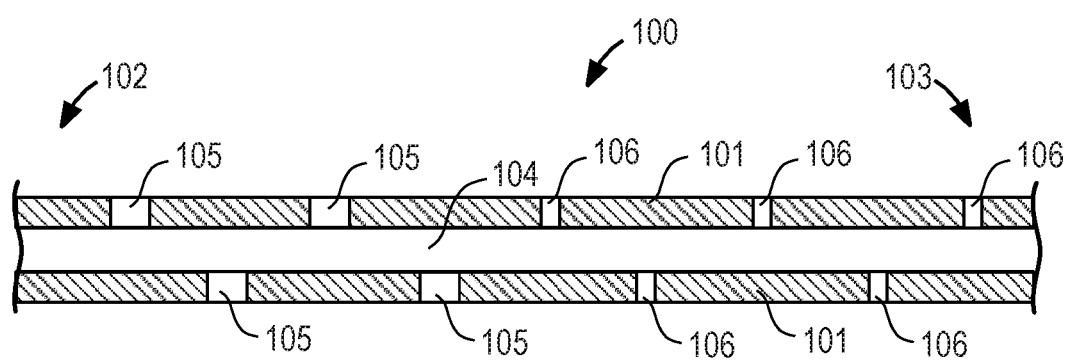
FIGS. 5-8 are sectional views of portions of various exemplary embodiments of inflow catheters with anti-clogging mechanisms suitable for use with the system of the present invention.

Referring to FIG. 5, inflow catheter 100 may be configured for use in the peritoneal cavity (and thus correspond to peritoneal catheter 23 of FIG. 1) or pleural or pericardial cavity, and preferably comprises tube 101 of medical-grade silicone including distal region 102, proximal region 103, lumen 104, a plurality of through-wall large holes 105, and a plurality of through wall small holes 106. Large holes 105 are sized larger than small holes 106 and holes 105, 106 have a suitable shape, e.g., circular, square, conical, or triangular holes. Preferably, large holes 105 are circular and have a diameter about twice the size of the diameter of small holes 106. Large holes 105 may be located in distal region 102 distal to small holes 106, located in proximal region 103. Fluid, e.g., peritoneal, pleural or pericardial fluid, from the body cavity is drawn into lumen 104 via large holes 105 and small holes 106 when suction is created within tube 101 by actuation of the pump in the implantable device. It is exceedingly important to prevent clogging and tissue ingrowth in the proximal holes because, if the proximal-most hole and accompanying lumen portion become clogged, the entire inflow catheter becomes clogged, rendering the more distal holes ineffective. Advantageously, small holes 106 are configured to be less prone to clogging as there will be lower hydraulic resistance at proximal region 103, as compared to large holes 105 in distal region 102, due to the smaller size of holes 106 and greater suction force through small holes 106. In an alternative embodiment, large holes 105 may be located in distal region 102 of inflow catheter 100 and small holes 106 may be located in proximal region 103 and holes varying in size between the size of small holes 106 and large holes 105 may be located between distal region 102 and proximal region 103 of inflow catheter 100 and may continuously increase in size moving from proximal region 103 to distal region 102.

Figure 6:
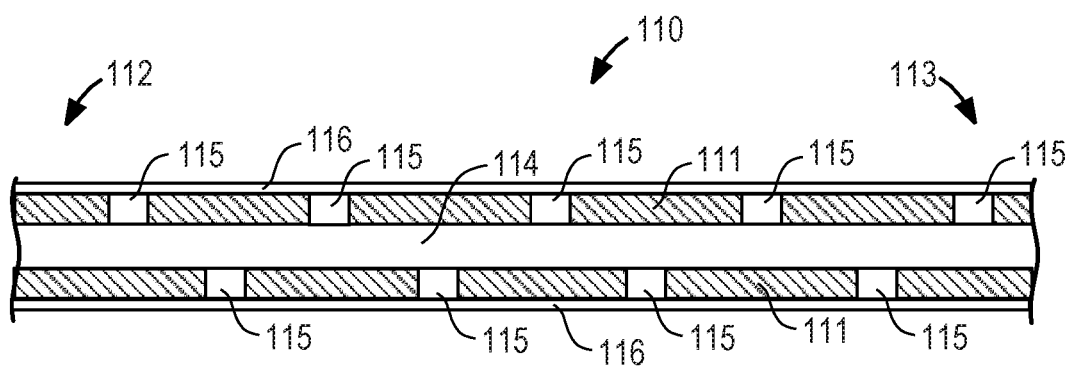

Referring now to FIG. 6, inflow catheter 110 may be configured for use in the peritoneal cavity (and thus correspond to peritoneal catheter 23 of FIG. 1) or pleural or pericardial cavity, and preferably comprises tube 111 of medical-grade silicone including distal region 112, proximal region 113, lumen 114, a plurality of through-wall holes 115, and mesh sleeve 116. Mesh sleeve 116 is disposed on an outer surface of tube 111, preferably over all holes 115, and is configured to permit fluid to flow therethrough, and into holes 115, and to filter out relatively large solid objects. Mesh sleeve 116 has a surface area and pore size suitable to allow a sufficient volume of fluid to pass therethrough, and also to reduce clogging due to solid objects entering holes 115 and/or lumen 114, or due to tissue ingrowth at holes 115 and/or lumen 114. Mesh sleeve 116 may include any suitable material known in the art, including a fabric, polymer, or flexible metal having pores of appropriate size to filter solid objects having diameters of, e.g., 20 µm or greater, or 50 µm or greater, or 100 µm or greater, or 150 µm or greater, or 200 µm or greater.

Figure 7:
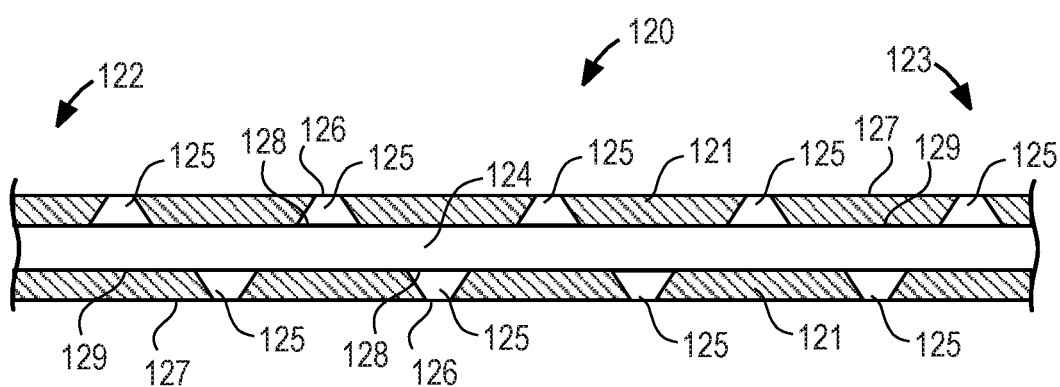

In FIG. 7, inflow catheter 120 may be configured for use in the peritoneal cavity (and thus correspond to peritoneal catheter 23 of FIG. 1) or pleural or pericardial cavity, and preferably comprises tube 121 of medical-grade silicone including distal region 122, proximal region 123, lumen 124, and a plurality of through-wall holes 125 having a truncated cone shape. Truncated cone holes 125 have small diameter portion 126 at outer surface 127 of tube 121 and large diameter portion 128 at inner surface 129 of tube 121. The truncated cone shape is expected to reduce clogging due to solid objects entering holes 125 and/or lumen 124 as large diameter portion 128 facilitates movement of solid objects through hole 125. In addition, the truncated cone shape is expected to reduce clogging due to tissue ingrowth at holes 125 and/or lumen 124 because such tissue would require more time to grow the distance of large diameter portion 128. In an alternative embodiment, inflow catheter 120 may include truncated cone holes 125 varying in size. For example, truncated cone holes 125 may continuously increase in size moving from proximal region 123 to distal region 122.

Figure 8:
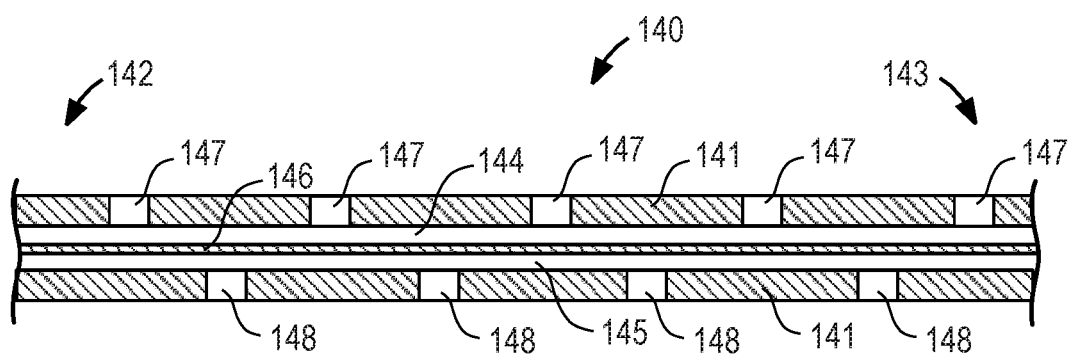

Referring now to FIG. 8, inflow catheter 140 may be configured for use in the peritoneal cavity (and thus correspond to peritoneal catheter 23 of FIG. 1) or pleural or pericardial cavity, and preferably comprises tube 141 of medical-grade silicone including distal region 142, proximal region 143, first lumen 144 separated from second lumen 145 via wall 146, and a plurality of through-wall holes 147, 148. Wall 146 may extend the full length or a partial length of tube 141 and preferably begins at a location proximal to where holes 147, 148 begin and extends past where holes 147, 148 end. Holes 147 permits fluid to flow into first lumen 144 while holes 148 permits fluid to flow into second lumen 145. Advantageously, if first lumen 144 becomes clogged, second lumen 145 remains functional, and vice versa, such that inflow catheter 140 does not need to be immediately replaced. It should be understood that while inflow catheter 140 is shown as having two lumens, it is not limited thereto. For example, an inflow catheter may have three, four, five or more lumens and multiplicities of through-wall holes corresponding to each lumen. Where the inflow catheter has more than one lumen, through-wall holes in each lumen may be distanced from one another. For example, a first lumen may have only distal holes and the second lumen may have only proximal holes.

As will be readily apparent to one of ordinary skill in the art, the anti-clogging mechanisms in the inflow catheter(s) described with respect to FIGS. 5-8 may be interchanged or used in combination. For example, an inflow catheter having through-holes with varied sizes may utilize a mesh sleeve, truncated cone-shaped holes, and/or more than one lumen. As another example, an inflow catheter having through-holes and a mesh sleeve may use truncated cone-shaped holes and/or more than one lumen. As yet another example, an inflow catheter having truncated cone-shaped holes may have more than one lumen.

Figure 9:
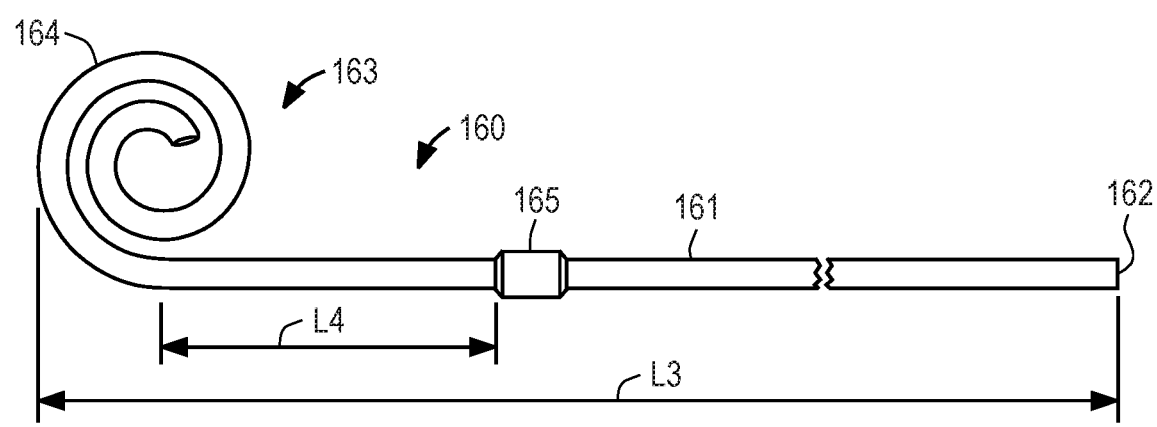
FIG. 9 is a side view of an embodiment of the outlet catheter suitable for use with the system of the present invention.

With respect to FIG. 9, an embodiment of outflow catheter 160 of the present invention is described, corresponding to bladder catheter 25 of FIG. 1. Outflow catheter 160 preferably comprises tube 161 of medical-grade silicone having inlet end 162 and outlet end 163 including spiral structure 164, and polyester ingrowth cuff 165. Outflow catheter 160 includes a single internal lumen that extends from inlet end 162 to a single outlet at the tip of spiral structure 164, commonly referred to as a "pigtail" design. Inlet end 162 may include a connector for securing the inlet end of the outflow catheter to implantable device 20, or may have a length that can be trimmed to fit a particular patient.

When configured for use as the outflow catheter in an ascites treatment system, outflow catheter may have length L3 of about 45 cm, with cuff 165 placed length L4 of about 5 to 6 cm from spiral structure 164. Outflow catheter 160 may be loaded onto a stylet with spiral structure 164 straightened, and implanted using a minimally invasive technique in which outlet end 163 and spiral structure 164 are passed through the wall of a patient's bladder using the stylet. When the stylet is removed, spiral structure 164 returns to the coiled shape shown in FIG. 9. Once outlet end 163 of outflow catheter 160 is disposed within the patient's bladder, the remainder of the catheter is implanted using a tunneling technique, such that inlet end 162 of the catheter may be coupled to implantable device 20. Spiral structure 164 may reduce the risk that outlet end 163 accidentally will be pulled out of the bladder before the tissue surrounding the bladder heals sufficiently to incorporate ingrowth cuff 165, thereby anchoring the outflow catheter in place.

In a preferred embodiment, the outflow catheter is configured to pass through a conventional peel-away sheath.

Outflow catheter 160 preferably is sufficiently resistant to torsional motion so as not to become twisted or kinked during or after implantation. In a preferred embodiment, inflow catheter(s) 90, 100, 110, 120, 140 and outflow catheter 160, and optionally anti-clog catheter described below, preferably are different colors, have different exterior shapes (e.g., square and round) or have different connection characteristics so that they cannot be inadvertently interchanged during connection to implantable device 20. Optionally, outflow catheter 160 may include an internal duckbill valve positioned midway between inlet 162 and outlet end 163 of the catheter to insure that urine does not flow from the bladder into the peritoneal cavity if the outflow catheter is accidentally pulled free from the pump outlet of implantable device 20.

In an alternative embodiment, the inflow, outflow, and/or anti-clog catheters may incorporate one or several anti-infective agents to inhibit the spread of infection between body cavities. Examples of anti-infective agents which may be utilized may include, e.g., bacteriostatic materials, bacteriocidal materials, one or more antibiotic dispensers, antibiotic eluting materials, coatings that prevent bacterial adhesion, and surface structure with antimicrobial effect and combinations thereof.

Alternatively, rather than comprising separate catheters, inflow, outflow, and/or anti-clog catheters may share a common wall. This arrangement may be utilized ideally for an ascites treatment embodiment because the bladder and peritoneal cavity share a common wall, thereby facilitating insertion of a single dual-lumen tube. In addition, any or all of the inflow or outflow or anti-clog catheters may be reinforced along a portion of its length or along its entire length using ribbon or wire braiding or lengths of wire or ribbon embedded or integrated within or along the catheters. The braiding or wire may be fabricated from metals such as stainless steels, superelastic metals such as nitinol, or from a variety of suitable polymers.

Figure 10:
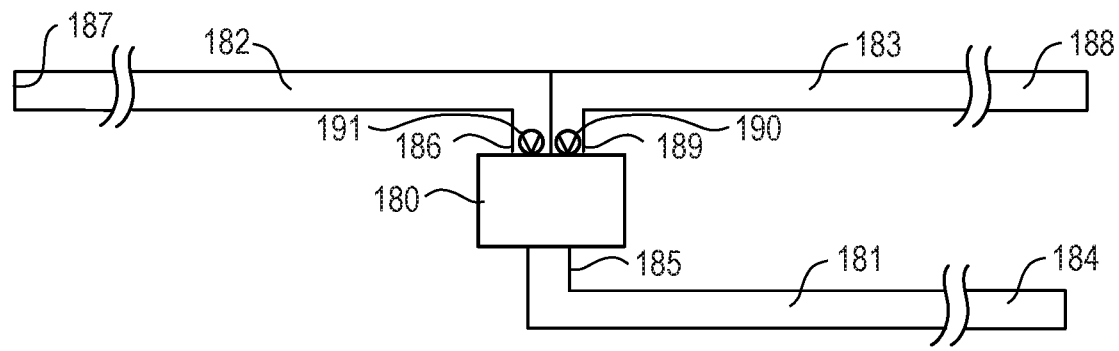
FIGS. 10 and 11 illustrate exemplary inflow, anti-clog, and outflow catheters and an implantable device suitable for use with the system of the present invention.

Referring now to FIG. 10, exemplary implantable components suitable for use with system 10 are described, including implantable housing 180, inflow catheter 181, outflow catheter 182, and anti-clog catheter 183. Implantable housing 180 contains a pump, a microcontroller, and connectors suitable for connection to catheters 181, 182, and 183. Implantable housing 180 preferably corresponds to housing 21 of FIG. 1 and thus detailed description thereof will be omitted for conciseness. Inflow catheter 181 has inlet end 184 and outlet end 185 and may be constructed similar to inflow catheter 90, 100, 110, 120, 140 of FIGS. 4-8. Inlet end 184 is adapted to be positioned within a body cavity, e.g., peritoneal cavity, pleural cavity, or pericardial cavity, and outlet end 185 is configured to be coupled to implantable housing 180. Outflow catheter 182 has inlet end 186 and outlet end 187 and may be constructed similar to outflow catheter 160 of FIG. 9. Inlet end 186 is configured to be coupled to implantable housing 180 and outlet end 187 is adapted to be positioned within a different body cavity, e.g., bladder, peritoneal cavity. Anti-clog catheter 183 has inlet end 188 and outlet end 189 and may be constructed similar to inflow catheter 90, 100, 110, 120, 140 of FIGS. 4-8. Inlet end 188 is adapted to be positioned within a body cavity, e.g., peritoneal cavity, pleural cavity, or pericardial cavity, and outlet end 189 is configured to be coupled to implantable housing 180. As will be appreciated by one skilled in the art, while outflow catheter 182 and anti-clog catheter 183 are illustrated as having a common wall, the invention is not limited thereto and each catheter may be completely separate.

Valve 190 is operatively associated with implantable housing 180 and anti-clog catheter 183 and may be disposed within housing 180 and/or anti-clog catheter 183. Valve 190 may be movable in response to commands sent by the microcontroller within implantable housing 180. For example, a programmed routine stored in memory associated with the microcontroller may command valve 190 to close during a time interval when the pump within housing 180 is actuated to move fluid into inlet end 184 through inflow catheter 181 toward outlet end 187 of outflow catheter 182 and to open during another time interval when the pump is actuated to move fluid in an opposite direction into inlet end 188 through anti-clog catheter 183 and out inlet end 184 of inflow catheter 181 to reduce potential clogging in inflow catheter 181. Alternatively, valve 190 may be a passive valve such as a duckbill valve.

In addition to, or in place of, valve 190, valve 191 is provided. Valve 191 is operatively associated with implantable housing 180 and outflow catheter 182 and may be disposed within housing 180 and/or outflow catheter 182. Valve 191 may be movable in response to commands sent by the microcontroller within implantable housing 180. For example, a programmed routine stored in memory associated with the microcontroller may command valve 191 to open during a time interval when the pump is actuated to move fluid into inlet end 184 through inflow catheter 181 toward outlet end 187 of outflow catheter 182 and to close during another time interval when the pump is actuated to move fluid in an opposite direction into inlet end 188 through anti-clog catheter 183 and out inlet end 184 of inflow catheter 181 to reduce potential clogging in inflow catheter 181. Valve 191 may be configured to prevent reverse flow from outflow catheter 182 to inflow catheter 181 or anti-clog catheter 183. In one embodiment, valve 191 is an internal duckbill valve positioned midway between inlet 186 and outlet end 187 of outflow catheter 182 to insure that urine does not flow from the bladder into the peritoneal cavity if outflow catheter 182 is accidentally pulled free from the pump outlet of implantable housing 180.

As described above, a non-transitory programmed routine may be stored in memory associated with the microcontroller within implantable housing 180. The programmed routine may be configured to selectably actuate the pump to move fluid from a body cavity in a first direction through inflow catheter 181 toward outlet end 187, in another body cavity, of outflow catheter 182 during a first time interval, and periodically to actuate valve 190 or 191 to place outlet end 189 of anti-clog catheter 183 in fluid communication with outlet end 185 of inflow catheter 181 and to actuate the pump to move fluid in a second direction through inflow catheter 181, opposite to the first direction, and out inlet end 184 of inflow catheter 181 to reduce potential clogging in inflow catheter 181. The inlet ends 184, 188 of catheters 181, 183 may be implanted in the same or different body cavities.

The routine may direct the pump to move fluid in the reverse direction (e.g., fluid moves into anti-clog catheter 183 and out inflow catheter 181) responsive to a predetermined passage of time (e.g., once a day), a predetermined number of pumping cycles (e.g., once every 10 cycles), or responsive to a condition indicative of clogging sensed by sensors (e.g., sensors 57-61 of FIG. 2) such as pressure above or below a predetermined pressure sensed in a body cavity, e.g., peritoneal cavity, pleural cavity, pericardial cavity, bladder. In this manner, there may be a source pressure sensor disposed within inflow catheter 181 and/or housing 180 configured to measure pressure of fluid within inflow catheter 181 (and thereby the pressure in the body cavity in which inlet end 184 is disposed), a sink pressure sensor disposed within outflow catheter 182 and/or housing 180 configured to measure pressure of fluid in outflow catheter 182 (and thereby the pressure in the body cavity in which outlet end 187 is disposed), and/or a pressure sensor disposed within anti-clog catheter 183 and/or housing 180 configured to measure pressure of fluid in anti-clog catheter 183 (and thereby the pressure in the body cavity in which inlet end 188 is disposed).

Figure 11:
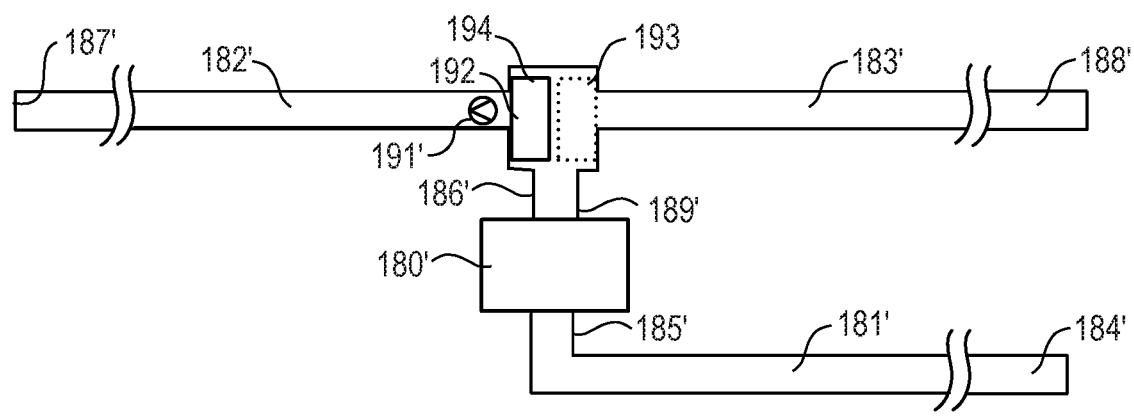

With respect to FIG. 11, additional exemplary implantable components suitable for use with system 10 are described, in which similar components are identified with like-primed numbers. As will be observed by comparing FIGS. 10 and 11, the implantable components of FIG. 11 include valve 192 rather than valve 190. Valve 192 is a mechanical valve and may be a monostable valve coupled to a motor in implantable housing via a mechanism, e.g., arm, configured to move the valve from first position 193 (shown in hidden lines), wherein anti-clog catheter 183' is blocked off from the pump, to second position 194, wherein outflow catheter 182' is blocked off from the pump, and back. Alternatively, valve 192 may be a bistable valve, such as the bistable valve available from Diener Precision Pumps Ltd. of Embrach, Switzerland, and is magnetic and configured to move from first position 193 to second position 194 and back responsive to magnetic fields received by an inductive coil disposed near valve 192 from another inductive coil in housing 180' or in charging and communication system 30. Preferably, valve 192 remains in first position 193 until the microcontroller commands the valve to move to second position 194. In first position 193, valve 192 permits fluid to move from inlet end 184' of inflow catheter 181' to outlet end 187' of outflow catheter 182' when the pump is actuated without flowing out anti-clog catheter 183'. Valve 191' may be configured to prevent reverse flow from outflow catheter 182' to inflow catheter 181'. For example, valve 191' may be an internal duckbill valve positioned within outflow catheter 182' to insure that urine does not flow from the bladder into the peritoneal cavity. In second position 194, valve 192 permits fluid to move from inlet end 188' of anti-clog catheter 183' to inlet end 184' of inflow catheter 181' when the pump is actuated in the opposite direction without creating suction in outflow catheter 182'.

Figure 12:
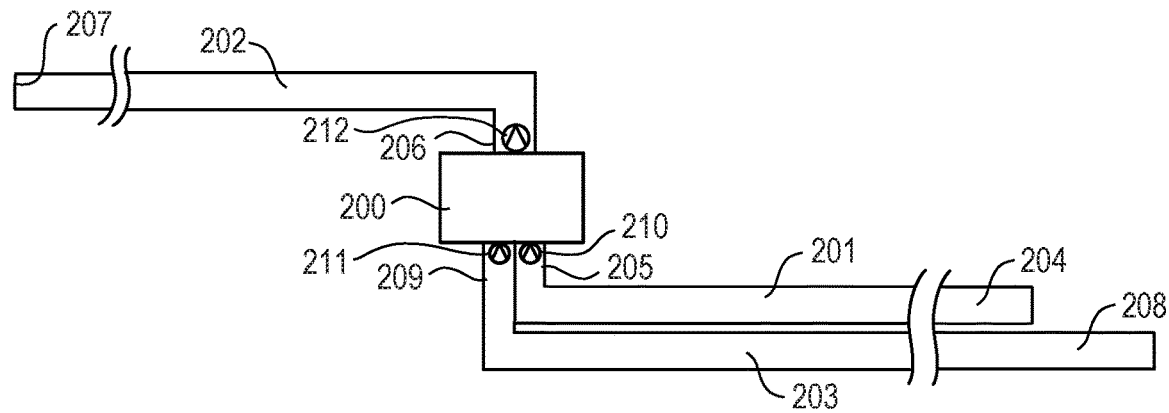
FIG. 12 illustrates exemplary first and second inflow catheters, an outflow catheter, and an implantable device suitable for use with the system of the present invention.

Referring now to FIG. 12, exemplary implantable components suitable for use with system 10 are described, including implantable housing 200, inflow catheter 201, outflow catheter 202, and inflow catheter 203. The embodiment of FIG. 12 may be particularly useful when a patient has fluid accumulation in more than one body cavity, e.g., peritoneal cavity, pleural cavity, and/or pericardial cavity. For example, it has been observed that ascites causes fluid buildup not only in the peritoneal cavity, but also in the pleural and/or pericardial cavities.

Implantable housing 200 contains a pump, a microcontroller, and connectors suitable for connection to catheters 201, 202, and 203. Implantable housing 200 preferably corresponds to housing 21 of FIG. 1 and thus detailed description thereof will be omitted for conciseness. Inflow catheter 201 has inlet end 204 and outlet end 205 and may be constructed similar to inflow catheter 90, 100, 110, 120, 140 of FIGS. 4-8. Inlet end 204 is adapted to be positioned within a body cavity, e.g., peritoneal cavity, pleural cavity, or pericardial cavity, and outlet end 205 is configured to be coupled to implantable housing 200. Outflow catheter 202 has inlet end 206 and outlet end 207 and may be constructed similar to outflow catheter 160 of FIG. 9. Inlet end 206 is configured to be coupled to implantable housing 200 and outlet end 207 is adapted to be positioned within a different body cavity, e.g., bladder, peritoneal cavity. Inflow catheter 203 has inlet end 208 and outlet end 209 and may be constructed similar to inflow catheter 90, 100, 110, 120, 140 of FIGS. 4-8. Inlet end 208 is adapted to be positioned within a third body cavity, e.g., peritoneal cavity, pleural cavity, or pericardial cavity, and outlet end 209 is configured to be coupled to implantable housing 200. Alternative inlet ends 204 and 208 of catheters 21 and 203 may be implanted in the same body cavity. As will be appreciated by one skilled in the art, while inflow catheter 201 and inflow catheter 203 are illustrated as having a common wall, the invention is not limited thereto and each catheter may be completely separate.

Valve 210 is operatively associated with implantable housing 200 and inflow catheter 201 and may be disposed within housing 200 and/or inflow catheter 201. Valve 210 may be movable in response to commands sent by the microcontroller within implantable housing 200. For example, a programmed routine stored in memory associated with the microcontroller may command valve 210 to close during a time interval when the pump within housing 200 is actuated to move fluid into inlet end 208 through inflow catheter 203 toward outlet end 207 of outflow catheter 202 and to open during another time interval when the pump is actuated to move fluid into inlet end 204 through inflow catheter 201 and out outlet end 207 of outflow catheter 202. The routine may cause the pump to move fluid from inlet end 204 of inflow catheter 201 to outlet end 207 of outflow catheter 202 and from inlet end 208 of inflow catheter 203 to outlet end 207 of outflow catheter 202 interchangeably and/or simultaneously.

In addition to, or in place of, valve 210, valve 211 is provided. Valve 211 is operatively associated with implantable housing 200 and inflow catheter 203 and may be disposed within housing 200 and/or inflow catheter 203. Valve 211 may be movable in response to commands sent by the microcontroller within implantable housing 200. For example, a programmed routine stored in memory associated with the microcontroller may command valve 211 to open during a time interval when the pump is actuated to move fluid into inlet end 208 through inflow catheter 203 toward outlet end 207 of outflow catheter 202 and to close during another time interval when the pump is actuated to move fluid into inlet end 204 through inflow catheter 201 and out outlet end 207 of outflow catheter 202.

Optional valve 212 is operatively associated with implantable housing 200 and outflow catheter 202 and may be disposed within housing 200 and/or outflow catheter 202. Valve 212 is configured to prevent reverse flow from outflow catheter 202 to inflow catheter 201 and/or inflow catheter 203. In one embodiment, valve 212 is an internal duckbill valve positioned midway between inlet 206 and outlet end 207 of outflow catheter 202 to insure that urine does not flow from the bladder into the peritoneal cavity if outflow catheter 202 is accidentally pulled free from the pump outlet of implantable housing 200.

As described above, a non-transitory programmed routine may be stored in memory associated with the microcontroller within implantable housing 200. The programmed routine may be configured to selectably actuate the pump to move fluid from a first body cavity through inflow catheter 201 toward outlet end 207, in a second body cavity, of outflow catheter 202 during a time interval, and periodically to actuate valve 210 or 211 to move fluid from a third body cavity through inflow catheter 203 toward outlet end 207 of outflow catheter 202 during the same time interval or a different time interval.

The routine may direct the pump to move fluid within inflow catheter 201 and/or inflow catheter 203 responsive to a predetermined passage of time (e.g., once every hour, once every half hour, once every hour while patient is sensed to be active), a predetermined number of pumping cycles (e.g., actuate valve 210 or 211 every other cycle), or responsive to a condition sensed by sensors (e.g., sensors 57-61 of FIG. 2) such as pressure above or below a predetermined pressure sensed in a body cavity, e.g., peritoneal cavity, pleural cavity, pericardial cavity, bladder. In this manner, there may be a source pressure sensor disposed within inflow catheter 201 and/or housing 200 configured to measure pressure of fluid within inflow catheter 201 (and thereby the first body cavity), a sink pressure sensor disposed within outflow catheter 202 and/or housing 200 configured to measure pressure of fluid in outflow catheter 202 (and thereby the second body cavity), and/or a pressure sensor disposed within inflow catheter 203 and/or housing 200 configured to measure pressure of fluid in inflow catheter 203 (and thereby the third body cavity).

Figure 13:
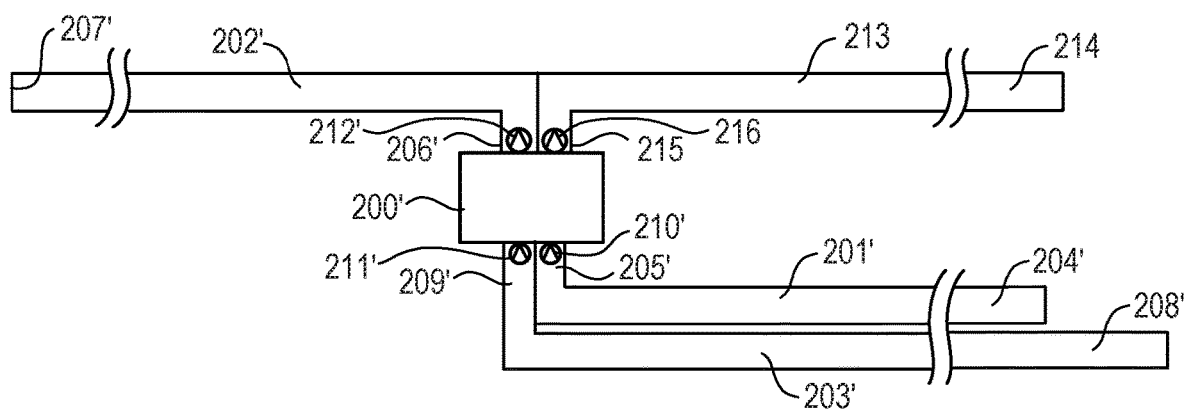
FIG. 13 illustrates exemplary first and second inflow catheters, an anti-clog catheter, an outflow catheter, and an implantable device suitable for use with the system of the present invention.

With respect to FIG. 13, additional exemplary implantable components suitable for use with system 10 are described, in which similar components are identified with like-primed numbers. As will be observed by comparing FIGS. 12 and 13, the implantable components of FIG. 13 further include anti-clog catheter 213. Anti-clog catheter 213 has inlet end 214 and outlet end 215 and may be constructed similar to inflow catheter 90, 100, 110, 120, 140 of FIGS. 4-8. Inlet end 214 is adapted to be positioned within the first or third body cavity, e.g., peritoneal cavity, pleural cavity, or pericardial cavity, and outlet end 215 is configured to be coupled to implantable housing 200'. As will be appreciated by one skilled in the art, while outflow catheter 202' and anti-clog catheter 213 are illustrated as having a common wall, the invention is not limited thereto and each catheter may be completely separate.

Valve 216 is operatively associated with implantable housing 200' and anti-clog catheter 213 and may be disposed within housing 200' and/or anti-clog catheter 213. Valve 216 may be movable in response to commands sent by the microcontroller within implantable housing 200'. For example, a programmed routine stored in memory associated with the microcontroller may command valve 216 to close during a time interval when the pump within housing 200' is actuated to move fluid into inlet end 204' and/or 208' through inflow catheter 201' and/or 203' toward outlet end 207' of outflow catheter 202' and to open during another time interval when the pump is actuated to move fluid in an opposite direction into inlet end 214 through anti-clog catheter 213 and out inlet end 204' and/or 208' of inflow catheter 201' and/or 203' to reduce potential clogging in inflow catheter 201' and/or 203'. During such an anti-clog cycle, the routine in the microcontroller may command valve 210' to open and valve 211' to close to move fluid from inlet end 214 out inlet end 204' to flush inflow catheter 201'; the routine may command valve 211' to open and valve 210' to close to move fluid from inlet end 214 out inlet end 208' to flush inflow catheter 203'; or the routine may command valve 210' and valve 211' to both open to move fluid from inlet end 214 out inlet ends 204' and 208' to flush inflow catheters 201' and 203'.

As described above, a non-transitory programmed routine may be stored in memory associated with the microcontroller within implantable housing 200'. The programmed routine may be configured to selectably actuate the pump to move fluid from a first body cavity through inflow catheter 201' toward outlet end 207', in a second body cavity, of outflow catheter 202' during a time interval, and periodically to actuate valve 210' or 211' to move fluid from a third body cavity through inflow catheter 203' toward outlet end 207' of outflow catheter 202' during the same time interval or a different time interval. The programmed routine further may be configured periodically to actuate valve 210', 211', and/or 216 to place outlet end 215 of anti-clog catheter 213 in fluid communication with outlet end 205' and/or 209' of inflow catheter 201' and/or 203' and to actuate the pump to move fluid in a reverse direction through anti-clog catheter 213 and out inlet end 204' and/or 208' of inflow catheter 201' and/or 203' to reduce potential clogging in inflow catheter 201' and/or 203'.

The routine may direct the pump to pump in the reverse direction (e.g., fluid moves into anti-clog catheter 213 and out inflow catheter 201' and/or 203') responsive to a predetermined passage of time (e.g., once a day), a predetermined number of pumping cycles (e.g., once every 10 cycles), or responsive to a condition indicative of clogging sensed by sensors (e.g., sensors 57-61 of FIG. 2) such as pressure above or below a predetermined pressure sensed in a body cavity, e.g., peritoneal cavity, pleural cavity, pericardial cavity, bladder. In this manner, there may be a pressure sensor disposed within anti-clog catheter 213 and/or housing 200' configured to measure pressure of fluid in anti-clog catheter 213 (and thereby the pressure in the body cavity in which inlet end 214 is disposed).

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed:

1. A fluid management system comprising:
  a first catheter having an inlet end adapted to be positioned within, open to, and in fluidic communication with a peritoneal cavity, and an outlet end;
  a second catheter having an inlet end adapted to be positioned within, open to, and in fluidic communication with the peritoneal cavity, and an outlet end;
  a third catheter having an inlet end and an outlet end adapted to be positioned in a second cavity;
  an implantable housing containing a pump, and a microcontroller, the housing coupled to the outlet end of the first catheter, the outlet end of the second catheter and the inlet end of the third catheter;
  a first valve operatively associated with the implantable housing and movable in response to the microcontroller, wherein the first valve is a monostable valve or a bistable valve; and
  a non-transitory programmed routine stored in memory associated with the microcontroller, the programmed routine configured to selectably actuate the pump to move ascites fluid from the peritoneal cavity in a first direction through the first catheter toward the outlet end of the third catheter during a first time interval, and periodically to actuate the first valve to place the outlet end of the second catheter in fluid communication with the outlet end of the first catheter and to actuate the pump to move ascites fluid from the peritoneal cavity into the inlet end of the second catheter and into the first catheter in a second direction through the first catheter, opposite to the first direction, and out the inlet end of the first catheter to reduce potential clogging in the first catheter.

2. The system of claim 1, wherein the outlet end of the third catheter is adapted to be positioned in a bladder.

3. The system of claim 1, further comprising a second valve operatively coupled to the third catheter and configured to prevent reverse flow from the third catheter to the first catheter or the second catheter.

4. The system of claim 3, wherein the second valve is a passive valve movable in response to a direction of flow.

5. The system of claim 1, wherein the programmed routine is configured to close the first valve during the first time interval when the pump is actuated to move fluid in the first direction through the first catheter toward the outlet end of the third catheter.

6. The system of claim 1, wherein the programmed routine is configured to open the first valve during the first time interval when the pump is actuated to move fluid in the first direction through the first catheter toward the outlet end of the third catheter.

7. The system of claim 1, wherein the second and third catheters are coupled together to create a Y-shaped catheter.

8. The system of claim 1, wherein the implantable housing further comprises a source pressure sensor configured to measure pressure of fluid within the first catheter and a sink pressure sensor configured to measure pressure of fluid in the third catheter.

9. The system of claim 8, wherein the implantable housing further comprises a pressure sensor configured to measure pressure of fluid within the second catheter.

10. The system of claim 1, wherein the pump comprises a gear pump coupled to an electric motor disposed within the implantable housing,
wherein, in the first direction, the gear pump rotates in a forward direction and, in the second direction, the gear pump rotates in a reverse direction.

11. The system of claim 1, wherein the first catheter comprises a plurality of through-holes configured to permit fluid in the peritoneal cavity to enter a lumen of the first catheter.

12. The system of claim 11, further comprising a mesh sleeve disposed on an outer surface of the first catheter, the mesh sleeve configured to permit fluid to flow therethrough and into the holes and to minimize solid objects from flowing therethrough.

13. The system of claim 11, wherein the holes have a truncated cone shape such that a smaller diameter portion of the truncated cone is disposed at an outer surface of the first catheter and a larger diameter portion of the truncated cone is disposed at an inner surface of the first catheter.

14. The system of claim 11, wherein the first catheter further comprises a second lumen, and
wherein a first portion of the holes permits fluid to flow into the lumen and a second portion of the holes permits fluid to flow into the second lumen.

15. The system of claim 1, further comprising a fourth catheter having an inlet end adapted to be positioned within a third cavity, and an outlet end coupled to the implantable housing.

16. A fluid management system comprising:
a first catheter having an inlet end adapted to be positioned within, open to, and in fluidic communication with a peritoneal cavity, and an outlet end;
a second catheter having an inlet end adapted to be positioned within, open to, and in fluidic communication with the peritoneal cavity, and an outlet end;
a third catheter having an inlet end and an outlet end adapted to be positioned in a second cavity;
an implantable housing containing a pump, and a microcontroller, the housing coupled to the outlet end of the first catheter, the outlet end of the second catheter and the inlet end of the third catheter;
a first valve operatively associated with the implantable housing and movable in response to the microcontroller;
a second valve operatively coupled to the third catheter and configured to prevent reverse flow from the third catheter to the first catheter or the second catheter, wherein the second valve is a passive valve movable in response to a direction of flow; and
a non-transitory programmed routine stored in memory associated with the microcontroller, the programmed routine configured to selectably actuate the pump to move ascites fluid from the peritoneal cavity in a first direction through the first catheter toward the outlet end of the third catheter during a first time interval, and periodically to actuate the first valve to place the outlet end of the second catheter in fluid communication with the outlet end of the first catheter and to actuate the pump to move ascites fluid from the peritoneal cavity into the inlet end of the second catheter and into the first catheter in a second direction through the first catheter, opposite to the first direction, and out the inlet end of the first catheter to reduce potential clogging in the first catheter.

17. A fluid management system comprising:
a first catheter having an inlet end adapted to be positioned within, open to, and in fluidic communication with a peritoneal cavity, and an outlet end, the first catheter comprising a plurality of through-holes configured to permit fluid in the peritoneal cavity to enter a lumen of the first catheter, the first catheter further comprising a second lumen, and wherein a first portion of the holes permits fluid to flow into the lumen and a second portion of the holes permits fluid to flow into the second lumen;
a second catheter having an inlet end adapted to be positioned within, open to, and in fluidic communication with the peritoneal cavity, and an outlet end;
a third catheter having an inlet end and an outlet end adapted to be positioned in a second cavity;
an implantable housing containing a pump, and a microcontroller, the housing coupled to the outlet end of the first catheter, the outlet end of the second catheter and the inlet end of the third catheter;
a first valve operatively associated with the implantable housing and movable in response to the microcontroller; and
a non-transitory programmed routine stored in memory associated with the microcontroller, the programmed routine configured to selectably actuate the pump to move ascites fluid from the peritoneal cavity in a first direction through the first catheter toward the outlet end of the third catheter during a first time interval, and periodically to actuate the first valve to place the outlet end of the second catheter in fluid communication with the outlet end of the first catheter and to actuate the pump to move ascites fluid from the peritoneal cavity into the inlet end of the second catheter and into the first catheter in a second direction through the first catheter, opposite to the first direction, and out the inlet end of the first catheter to reduce potential clogging in the first catheter.

* * * * *

UNITED STATES PATENT AND TRADEMARK OFFICE
CERTIFICATE OF CORRECTION

PATENT NO. : 10,716,922 B2
APPLICATION NO. : 15/249192
DATED : July 21, 2020
INVENTOR(S) : Thomas Werner Degen and Noel L. Johnson Page 1 of 1

It is certified that error appears in the above-identified patent and that said Letters Patent is hereby corrected as shown below:

On the Title Page

Under APPLICANTS, item (71), Lines 2 and 3:
Delete "Christopher C. Bolten, San Diego, CA (US)"

Signed and Sealed this
Tenth Day of November, 2020

Andrei Iancu
*Director of the United States Patent and Trademark Office*